US007879319B2

(12) United States Patent
Gillies et al.

(10) Patent No.: US 7,879,319 B2
(45) Date of Patent: *Feb. 1, 2011

(54) HETERODIMERIC FUSION PROTEINS USEFUL FOR TARGETED IMMUNE THERAPY AND GENERAL IMMUNE STIMULATION

(75) Inventors: Stephen D. Gillies, Carlisle, MA (US); Kin-Ming Lo, Lexington, MA (US); Yan Lan, Belmont, MA (US)

(73) Assignee: Merk Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/498,491

(22) Filed: Jul. 7, 2009

(65) Prior Publication Data

US 2010/0015089 A1    Jan. 21, 2010

Related U.S. Application Data

(60) Division of application No. 11/804,895, filed on May 21, 2007, now Pat. No. 7,576,193, which is a continuation of application No. 10/935,532, filed on Sep. 7, 2004, now Pat. No. 7,226,998, which is a continuation of application No. 10/005,212, filed on Dec. 4, 2001, now Pat. No. 6,838,260, which is a continuation of application No. 08/986,997, filed on Dec. 8, 1997, now abandoned.

(51) Int. Cl.
*A61K 38/19* (2006.01)
*A61K 38/20* (2006.01)
(52) U.S. Cl. .................. 424/85.1; 424/85.2; 424/178.1
(58) Field of Classification Search ........................ None
See application file for complete search history.

(56) References Cited

U.S. PATENT DOCUMENTS

| | | | |
|---|---|---|---|
| 4,196,265 A | 4/1980 | Koprowski et al. |
| 4,469,797 A | 9/1984 | Albarella |
| 4,676,980 A | 6/1987 | Segal et al. |
| 4,703,008 A | 10/1987 | Lin |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,073,627 A | 12/1991 | Curtis et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,457,038 A | 10/1995 | Trinchieri et al. |
| 5,480,981 A | 1/1996 | Goodwin et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,639,725 A | 6/1997 | O'Reilly et al. |
| 5,645,835 A | 7/1997 | Fell, Jr. et al. |
| 5,650,150 A | 7/1997 | Gillies |
| 5,650,492 A | 7/1997 | Gately et al. |
| 5,667,776 A | 9/1997 | Zimmerman et al. |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,712,120 A | 1/1998 | Rodriguez et al. |
| 5,719,266 A | 2/1998 | DiMarchi et al. |
| 5,723,125 A | 3/1998 | Chang et al. |
| 5,726,044 A | 3/1998 | Lo et al. |
| 5,728,552 A | 3/1998 | Fujisawa et al. |

(Continued)

FOREIGN PATENT DOCUMENTS

AU    2172588    3/1989

(Continued)

OTHER PUBLICATIONS

Abaza et al., (1992) "Effects of Amino Acid Substitutions Outside an Antigenic Site on Protein Binding to Monoclonal Antibodies of Predetermined Specificity Obtained by Peptide Immunization" Journal of Protein Chemistry, vol. 11, No. 5: pp. 433-444.

(Continued)

*Primary Examiner*—Prema Mertz
(74) *Attorney, Agent, or Firm*—Goodwin Procter LLP

(57) ABSTRACT

Disclosed are methods for producing fusion proteins with the heterodimeric cytokine, interleukin-12. In order to insure that the proper ratio of fused and non-fused subunits are obtained in the fusion protein, a specific stepwise approach to genetic engineering is used. This consists of first expressing the non-fused p40 IL-12 subunit in a production cell line, followed by or simultaneously expressing in the same cell, a second recombinant fusion protein consisting of the fused polypeptide linked by a peptide bond to the p35 subunit of IL-12. Molecules containing the p35 fusion protein cannot be secreted from the transfected mammalian cell without first complexing in a one to one ratio with the p40 subunit, thus ensuring the production of active heterodimeric fusion proteins.

3 Claims, 9 Drawing Sheets

U.S. PATENT DOCUMENTS

| | | | |
|---|---|---|---|
| 5,733,876 | A | 3/1998 | O'Reilly et al. |
| 5,756,349 | A | 5/1998 | Lin |
| 5,756,461 | A | 5/1998 | Stephens |
| 5,759,551 | A | 6/1998 | Ladd et al. |
| 5,770,195 | A | 6/1998 | Hudziak et al. |
| 5,800,810 | A | 9/1998 | Doyle et al. |
| 5,807,715 | A | 9/1998 | Morrison et al. |
| 5,827,516 | A | 10/1998 | Urban et al. |
| 5,827,703 | A | 10/1998 | Debs et al. |
| 5,837,682 | A | 11/1998 | Folkman et al. |
| 5,837,821 | A | 11/1998 | Wu |
| 5,843,423 | A | 12/1998 | Lyman et al. |
| 5,854,205 | A | 12/1998 | O'Reilly et al. |
| 5,856,298 | A | 1/1999 | Strickland |
| 5,858,347 | A | 1/1999 | Bauer et al. |
| 5,885,795 | A | 3/1999 | O'Reilly et al. |
| 5,886,178 | A | 3/1999 | Allen et al. |
| 5,888,772 | A | 3/1999 | Okasinski et al. |
| 5,888,773 | A | 3/1999 | Jost et al. |
| 5,891,680 | A | 4/1999 | Lieschke et al. |
| 5,908,626 | A | 6/1999 | Chang et al. |
| 5,922,685 | A | 7/1999 | Rakhmilevich et al. |
| 5,955,422 | A | 9/1999 | Lin |
| 5,994,104 | A | 11/1999 | Anderson et al. |
| 5,994,126 | A | 11/1999 | Steinman et al. |
| 6,080,409 | A | 6/2000 | Laus et al. |
| 6,086,875 | A | 7/2000 | Blumberg et al. |
| 6,100,387 | A | 8/2000 | Herrmann et al. |
| 6,169,070 | B1 | 1/2001 | Chen et al. |
| 6,171,588 | B1 | 1/2001 | Carron et al. |
| 6,231,536 | B1 | 5/2001 | Lentz |
| 6,277,375 | B1 | 8/2001 | Ward |
| 6,284,536 | B1 | 9/2001 | Morrison et al. |
| 6,291,158 | B1 | 9/2001 | Winter et al. |
| 6,335,176 | B1 | 1/2002 | Inglese et al. |
| 6,340,742 | B1 | 1/2002 | Burg et al. |
| 6,348,192 | B1 | 2/2002 | Chan et al. |
| 6,406,689 | B1 | 6/2002 | Falkenberg et al. |
| 6,429,199 | B1 | 8/2002 | Krieg et al. |
| 6,444,792 | B1 | 9/2002 | Gray et al. |
| 6,475,717 | B1 | 11/2002 | Enssle et al. |
| 6,485,726 | B1 | 11/2002 | Blumberg et al. |
| 6,500,641 | B1 | 12/2002 | Chen et al. |
| 6,506,405 | B1 | 1/2003 | Desai et al. |
| 6,551,592 | B2 | 4/2003 | Lindhofer et al. |
| 6,583,272 | B1 | 6/2003 | Bailon |
| 6,586,398 | B1 | 7/2003 | Kinstler et al. |
| 6,617,135 | B1 | 9/2003 | Gillies et al. |
| 6,620,413 | B1 | 9/2003 | DeSauvage et al. |
| 6,627,615 | B1 | 9/2003 | Debs et al. |
| 6,646,113 | B1 | 11/2003 | Dreyfuss et al. |
| 6,750,329 | B1 | 6/2004 | Rosenblum et al. |
| 6,838,260 | B2 * | 1/2005 | Gillies et al. ............. 435/69.51 |
| 7,141,151 | B2 | 11/2006 | Habets et al. |
| 7,141,651 | B2 | 11/2006 | Gillies et al. |
| 7,226,998 | B2 | 6/2007 | Gillies et al. |
| 7,576,193 | B2 | 8/2009 | Gillies et al. |
| 7,582,288 | B2 * | 9/2009 | Gillies et al. ............... 424/85.1 |
| 2001/0053539 | A1 | 12/2001 | Lauffer et al. |
| 2002/0037558 | A1 | 3/2002 | Lo et al. |
| 2002/0081664 | A1 | 6/2002 | Lo et al. |
| 2002/0142374 | A1 | 10/2002 | Gallo et al. |
| 2002/0146388 | A1 | 10/2002 | Gillies |
| 2002/0147311 | A1 | 10/2002 | Gillies et al. |
| 2002/0192222 | A1 | 12/2002 | Blumberg et al. |
| 2002/0193570 | A1 | 12/2002 | Gillies et al. |
| 2003/0003529 | A1 | 1/2003 | Bayer |
| 2003/0012789 | A1 | 1/2003 | Blumberg et al. |
| 2003/0044423 | A1 | 3/2003 | Gillies et al. |
| 2003/0049227 | A1 | 3/2003 | Gillies et al. |
| 2003/0105294 | A1 | 6/2003 | Gillies et al. |
| 2003/0139365 | A1 | 7/2003 | Lo et al. |
| 2003/0139575 | A1 | 7/2003 | Gillies |
| 2003/0157054 | A1 | 8/2003 | Gillies et al. |
| 2003/0166163 | A1 | 9/2003 | Gillies |
| 2003/0166877 | A1 | 9/2003 | Gillies et al. |
| 2004/0013640 | A1 | 1/2004 | Zardi et al. |
| 2004/0033210 | A1 | 2/2004 | Gillies |
| 2004/0043457 | A1 | 3/2004 | Schumacher et al. |
| 2004/0053366 | A1 | 3/2004 | Lo et al. |
| 2004/0072299 | A1 | 4/2004 | Gillies et al. |
| 2004/0082039 | A1 | 4/2004 | Gillies et al. |
| 2004/0180035 | A1 | 9/2004 | Gillies |
| 2004/0180386 | A1 | 9/2004 | Carr et al. |
| 2004/0203100 | A1 | 10/2004 | Gillies et al. |
| 2005/0069521 | A1 | 3/2005 | Gillies et al. |

FOREIGN PATENT DOCUMENTS

| | | |
|---|---|---|
| CN | 93100115.3 | 7/1993 |
| CN | 931001153 | 7/1993 |
| DE | 3712985 | 11/1988 |
| EP | 0158198 | 10/1985 |
| EP | 0211769 | 2/1987 |
| EP | 0237019 | 9/1987 |
| EP | 0256714 | 2/1988 |
| EP | 0294703 | 12/1988 |
| EP | 0308936 | 3/1989 |
| EP | 0314317 | 5/1989 |
| EP | 0318554 | 6/1989 |
| EP | 0319012 | 6/1989 |
| EP | 0326120 | 8/1989 |
| EP | 0344134 | 11/1989 |
| EP | 0350230 | 1/1990 |
| EP | 0375562 | 6/1990 |
| EP | 0396387 | 11/1990 |
| EP | 0428596 | 5/1991 |
| EP | 0433827 | 6/1991 |
| EP | 0439095 | 7/1991 |
| EP | 0511747 | 11/1992 |
| EP | 0519596 | 12/1992 |
| EP | 0601043 | 6/1994 |
| EP | 0640619 | 3/1995 |
| EP | 0668353 | 8/1995 |
| EP | 0699755 | 3/1996 |
| EP | 0706799 | 4/1996 |
| EP | 0790309 | 8/1997 |
| EP | 1088888 | 4/2001 |
| GB | 2188638 | 10/1987 |
| GB | 2292382 | 2/1996 |
| JP | 63267278 | 11/1988 |
| JP | 63267296 | 11/1988 |
| JP | 3712985 | 11/2005 |
| WO | WO-8601533 | 3/1986 |
| WO | WO-8800052 | 1/1988 |
| WO | WO-8809344 | 12/1988 |
| WO | WO-8902922 | 4/1989 |
| WO | WO-8909620 | 10/1989 |
| WO | WO-9003801 | 4/1990 |
| WO | WO-9100360 | 1/1991 |
| WO | WO-9104329 | 4/1991 |
| WO | WO-9108298 | 6/1991 |
| WO | WO-9113166 | 9/1991 |
| WO | WO-9114438 | 10/1991 |
| WO | WO-9202240 | 2/1992 |
| WO | WO-9208495 | 5/1992 |
| WO | WO-9208801 | 5/1992 |
| WO | WO-9210755 | 6/1992 |
| WO | WO-9216562 | 10/1992 |
| WO | WO-9303157 | 2/1993 |
| WO | WO-9310229 | 5/1993 |
| WO | WO-9320185 | 10/1993 |
| WO | WO-9424160 | 10/1994 |
| WO | WO-9425055 | 11/1994 |

| WO | WO-9505468 | 2/1995 |
| WO | WO-9521258 | 8/1995 |
| WO | WO-9528427 | 10/1995 |
| WO | WO-9531483 | 11/1995 |
| WO | WO-9604388 | 2/1996 |
| WO | WO-9605309 | 2/1996 |
| WO | WO-9608570 | 3/1996 |
| WO | WO-9618412 | 6/1996 |
| WO | WO-9631526 | 10/1996 |
| WO | WO-9640792 | 12/1996 |
| WO | WO-9700317 | 1/1997 |
| WO | WO-9700319 | 1/1997 |
| WO | WO-9715666 | 5/1997 |
| WO | WO-9720062 | 6/1997 |
| WO | WO-9724137 | 7/1997 |
| WO | WO-9724440 | 7/1997 |
| WO | WO-9726335 | 7/1997 |
| WO | WO-9730089 | 8/1997 |
| WO | WO-9733617 | 9/1997 |
| WO | WO-9733619 | 9/1997 |
| WO | WO-9734631 | 9/1997 |
| WO | WO-9773316 | 11/1997 |
| WO | WO-9800127 | 1/1998 |
| WO | WO-9806752 | 2/1998 |
| WO | WO-9828427 | 7/1998 |
| WO | WO-9830706 | 7/1998 |
| WO | WO-9846257 | 10/1998 |
| WO | WO-9859244 | 12/1998 |
| WO | WO-9902709 | 1/1999 |
| WO | WO-9903887 | 1/1999 |
| WO | WO-9929732 | 6/1999 |
| WO | WO-9943713 | 9/1999 |
| WO | WO-9952562 | 10/1999 |
| WO | WO-9953958 | 10/1999 |
| WO | WO-9960128 | 11/1999 |
| WO | WO-9962944 | 12/1999 |
| WO | WO-9966054 | 12/1999 |
| WO | WO-0011033 | 3/2000 |
| WO | WO-0024893 | 5/2000 |
| WO | WO-0034317 | 6/2000 |
| WO | WO-0040615 | 7/2000 |
| WO | WO-0068376 | 11/2000 |
| WO | WO-0069913 | 11/2000 |
| WO | WO-0078334 | 12/2000 |
| WO | WO-0107081 | 2/2001 |
| WO | WO-0110912 | 2/2001 |
| WO | WO-0136489 | 5/2001 |
| WO | WO-0158957 | 8/2001 |
| WO | WO-0202143 | 1/2002 |
| WO | WO-02066514 | 8/2002 |
| WO | WO-02072605 | 9/2002 |
| WO | WO-02079232 | 10/2002 |
| WO | WO-02079415 | 10/2002 |
| WO | WO-02090566 | 11/2002 |
| WO | WO-03015697 | 2/2003 |
| WO | WO-03048334 | 6/2003 |
| WO | WO-03077834 | 9/2003 |

OTHER PUBLICATIONS

Abstract XP-002116766, (1996) "Prostaglandins, their inhibitors and cancer" Prostaglandins, Leukotrienes and Essential Fatty Acids, vol. 54, No. 2, pp. 83-94.
Arenberg et al. (1996) "Interferon-γ-inducible Protein 10 (IP-10) Is an Angiostatic Factor That Inhibits Human Non-small Cell Lung Cancer (NSCLC) Tumorigenesis and Spontaneous Metastases," J. Exp. Med,. vol. 184, pp. 981-992.
Bacha et al., (1988). "Interleukin 2 Receptor-Targeted Cytotoxicity Interleukin 2 Receptor-mediated Action of a Diphtheria Toxin-related Interleukin 2 Fusion Protein", J. Experimental Medicine, vol. 167, pp. 612-622.
Bachelot et al., (Mar. 1998) "Retrovirus-Mediated Gene Transfer of an Angiostatin-Endostatin Fusion protein with Enhanced Anti-Tumor Properties In Vivo", Proceedings of the Annual Meeting of the American Association for Cancer Research, vol. 39, pp. 271, Abstract # 1856.
Barnett et al. (1994) "Purification, characterization and selective inhibition of human prostaglandin G/H synthase 1 and 2 expressed in the baculovirus system," Biochimica et Biophysica Acta, 1209:130-139.
Baselga, et al (1998) "Recombinant Humanized Anti-HER2 Antibody (Herceptin.TM.) Enhances the Antitumor activity of Paclitazel and Doxorubicin against HER3/neu Overexpressing Human Breast Cancer Xenografts." Cancer Research, vol. 58, pp. 2825-2831.
Batova et al., (1999), "The Ch 14.18-GM-CSF Fusion Protein Is Effective at Mediating Antibody-dependent Cellular Cytotoxicity and Complement-dependent Cytotoxicity in Vitro," Clinical Cancer Research, vol. 5, No. 12, pp. 4259-4263.
Becker et al., (1996), "Eradication of human hepatic and pulmonary melanoma metastases in SCID mice by antibody-interleukin 2 fusion proteins," Proc. Natl. Acad. Sci. USA, vol. 93, pp. 2702-2707.
Beutler et al., (1988) "Tumor Necrosis, Cachexia, Shock, and Inflammation: A Common Mediator", Ann. Rev. Biochem., vol. 57, pp. 505-518.
Bjorn et al., (1985), "Evaluation of Monoclonal Antibodies for the Development of Breast Cancer Immunotoxins" Cancer Research, vol. 45, pp. 1214-1221.
Boehm et al. (1997) "Antiangiogenic therapy of experimental cancer does not induce acquired drug resistance," Letters to Nature, vol. 390, pp. 404-407.
Boehm et al., (1998), "Zinc-Binding of Endostatin Is Essential for Its Antiangiogenic Activity," Biochemical and Biophysical Research Communications, vol. 252, pp. 190-194.
Brooks et al. (1994), "Integrin $\alpha_v\beta_3$ Antagonists Promote Tumor Regression by Inducing Apoptosis of Angiogenic Blood Vessels," Cell, vol. 79, pp. 1157-1164.
Burgess et al., (1990), "Possible Dissociation of the heparin-binding and Mitogenic Activities of Heparin-binding (Acidic Fibroblast) Growth Factor-1 from Its Receptor-binding Activities by Site-directed Mutagenesis of a Single Lysine Residue, "Journal of Cell Biology, vol. 111, pp. 2129-2138.
Canfield et al. (1991), "The Binding Affinity of Human IgG for its High Affinity Fc Receptor is Determined by Multiple Amino Acids in the CH2 Domain and Is Modulated by the Hinge Region," Journal of Experimental Medicine, vol. 173, No. 6, pp. 1483-1491.
Cao et al., (1996), "Kringle Domains of Human Angiostatin," The Journal of Biological Chemistry, vol. 271, No. 46, pp. 29461-29467.
Cao et al. (1997), "Kringle 5 of Plasminogen is a Novel Inhibitor of Endothelial Cell Growth," The Journal of Biological Chemistry, vol. 272, No. 36, pp. 22924-22928.
Capon et al. (1989), "Designing CD4 immunoadhesins for AIDS therapy," Nature, vol. 337, pp. 525-531.
Chan et al., (1991) "Induction of Interferon γ Production by Natural Killer Cell Stimulatory Factor: Characterization of the Responder Cells and Synergy with Other Inducers," J. Exp. Med., pp. 869-879.
Chang et al., (1989), "Overview of Interleukin-2 as an Immunotherapeutic Agent," Seminars in Surgical Oncology, vol. 5, pp. 385-390.
Chaudhary et al., (1989), "A recombinant immunotoxin consisting of two antibody variable domains fused to *Pseudomonas* exotoxin" Nature, vol. 339, pp. 394-397.
Chaudhary et al., (1988), "Selective killing of HIV-infected cells by recombinant human CD4-*Pseudomonas* exotoxin hybrid protein," Nature, vol. 335, pp. 370-372.
Chen et al., (1997), "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," Journal of Immunology, vol. 159,No. 1, pp. 351-358.
Cheon et al. (1994) "High-affinity binding sites for related fibroblast growth factor ligands reside within different receptor immunoglobulin-like domains," Proc. Natl. Acad. Sci. USA 91: 989-993.
Cohen, S. L. et al., (Aug. 15, 1996), "Human leptin characterization," Nature, vol. 382, p. 589.

Cole et al. (1997) "Human IgG2 Variants of Chimeric Anti-CD3 Are Nonmitogenic to T Cells," Journal of Immunology, vol. 159, pp. 3613-3621.

Colombo et al., (1996), "Amount of Interleukin 12 Available at the Tumor Site is Critical for Tumor Regression," Cancer Research, vol. 56, pp. 2531-2534.

D'Amato et al., (1994), "Thalidomide is an inhibitor of angiogenesis," Proc. Natl. Acad. Sci. USA, vol. 91, pp. 4082-4085.

D'Andrea et al., (1992), "Production of Natural Killer Cell Stimulatory Factor (Interleukin 12) by Peripheral Blood Mononuclear Cells," J. Exp. Med., vol. 176, pp. 1387-1398.

Ding et al., (Sep. 1988), "Zinc-Dependent Dimers Observed in Crystals of Human Edostatin," Proceedings of the National Academy of Sciences of USA, vol. 95, No. 18, pp. 10443-10448.

Earnest et al., (1992), "Piroxicam and Other Cyclooxygenase Inhibitors: Potential for Cancer Chemoprevention," J. Cell. Biochem. Supp, vol. 161, pp. 156-166.

Eisenthal, (1990) "Indomethacin up-regulated the generation of lymphokine-activated killer-cell activity and antibody-dependent cellular cytotoxicity mediated by interleukin-2," Cancer Immunol. Immunotherap. vol. 31, pp. 342-348.

Fell et al., (1991), "Genetic Construction and Characterization of Fusion Protein Consisting of a Chimeric F(ab') with Specificity for Carcinomas and Human IL-2," The J. of Immunology, vol. 146, pp. 2446-2452.

Friedman, J. M. et al., (Oct. 22, 1998). "Leptin and the regulation of body weight in mammals," Nature, vol. 395, pp. 763-770.

Gasson et al., (1984), "Purified Human Granulocyte Macrophage Colony-Stimulating Factor: Direct Action in Neutrophils", Science, vol. 226, pp. 1339-1134.

Gately et al., (1998), "The Interleuking-12/Interleukin-12 Receptor system: Role in Normal and Pathologic Immune Responses" Annu. Rev. Immunol., vol. 16, pp. 495-521.

Gillessen et al., (1995), "Mouse Interleukin-12 (IL-12) p40 Homodimer: A Potent IL-12 Antagonist" Eur. J. Immunol., vol. 25, pp. 200-206.

Gillies et al. (1990), "Antigen binding and biological activities of engineered mutant chimeric antibodies with human tumor specificities," Hum. Antibod. Hybridomas vol. 1, No. 1, pp. 47-54.

Gillies et al., (1989), "High-Level Expression of Chimeric Antibodies Using Adapted cDNA Variable Region Cassettes," J. Immunol. Methods, vol. 125, pp. 191-202.

Gillies et al., (1992), "Antibody-Targeted Interleukin 2 Stimulates T-Cell Killing of Autologous Tumor Cells," Proc. Natl. Acad. Science, vol. 89, pp. 1428-1432.

Gillies et al., (1993), "Biological Activity and In Vivo Clearance of Antitumor Antibody/Cytokine Fusion Proteins," Bioconjugate Chem., vol. 4, pp. 230-235.

Gillies, et al., (Jun. 1998), "Antibody-IL-12 fusion proteins are effective in SCID mouse models of prostrate and colon carcinoma metastases," Journal Immunology, vol. 160, No. 12, pp. 6195-6203.

Gillies, et al., (May 1999), "Improving the efficacy of antibody-interleukin 2 fusion proteins by reducing their interaction with Fc receptors," Cancer Research, vol. 59, No. 9, pp. 2159-2166.

Gillies et al., (1989), "Expression of Human Anti-Tetanus toxoid antibody in Transfected Murine Myeloma Cells," Bio/Technology, vol. 7, pp. 799-804.

Gillis et al., (1978), "T Cell Growth Factor: Parameters of Production and a Quantitative Microassay for Activity," Journal of Immunology, vol. 120, No. 6, pp. 2027-2032.

Goeddel et al., (1986), "Tumor Necrosis Factors; Gene Structure and Biological Activities," Pharm. Sciences, pp. 597-609.

Gren et al., (1983), "A New Type of Leukocytic Interferon,".. Dokl. Biochem., vol. 269, pp. 91-95.

Grimaldi et al., (1989), "The t(5;14) Chromosomal Translocation in a Case of Acute Lymphocytic Leukemia Joins the Interleukin-3 Gene to the Immunoglobulin Heavy Chain Gene," Blood, vol. 73, No. 8, pp. 2081-2805.

Guyre et al., (1997), "Increased potency of Fc-receptor-targeted antigens," Cancer Immunol. Immunother. vol. 45, pp. 146-148.

Harris et al., "Therapeutic Antibodies—the Coming of Age" Tibtech, 11:42-44 (Feb. 1993).

Harvill et al. (Oct. 1996), "In vivo properties of an IgG3-IL-2 fusion protein: A general strategy for immune potentiation." Journal of Immunology, vol. 157, No. 7, pp. 3165-3170.

Hazama et al., (1993), "Adjuvant-Independent Enhanced Immune Responses to Recombinant Herpes Simplex Virus Type 1 Glycoprotein D by Fusion with Biologically Active Interleukin-2," Vaccine, vol. 11, Issue 6, pp. 629-636.

He et al. (1998) "Humanization and Pharmacokinetics of Monoclonal Antibody with Specificity for Both E- and P-Selectin," J. Immunol. 1029-1035.

Heinzel et al., (1997), "In Vivo Production and Function of IL-12 p40 Homodimers In Vivo Biology of IL-12 p40 Homodimer," Journal of Immunology, vol. 158, pp. 4381-4388.

Hellstrom et al., (1986), "Antitumor effects of L6, an IgG2a antibody that reacts with most human carcinomas," Proc. Natl. Acad. Sci. USA, vol. 83, No. 18, pp. 7059-7063.

Henkart, (1985), "Mechanism of Lymphocyte-Mediated Cytotoxicity," Ann. Rev. Immunol., vol. 3, pp. 31-58.

Herrmann et al., (1989), "Hematopoeitic Responses With Advanced Malignancy Treated With Recombinant Human Granulocyte-Macrophage Colony-Stimulating Factor," Journal of Clinical Oncology, vol. 7, No. 2, pp. 159-167.

Hohenester et al., (1998), "Crystal Structure of the Angiogenesis Inhibitor Endostatin at 1/5 Å Resolution," EMBO Journal, vol. 17, No. 6, pp. 1656-1664.

Holden, et al. (2001) "Augmentation of Anti-Tumor Activity of KS-IL2 Immunocytokine with Chemotherapeutic Agents." Proceedings of the American Association for Cancer Research, vol. 42, p. 683.

Holden, et al. (2001) "Augmentation of Antitumor activity of an Antibody-Interleukin 2 Immunocytokine with Chemotherapeutic Agents" Clinical Cancer Research; vol. 7, No. 9, pp. 2862-2869.

Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," Biochim. and Biophys. Acta, vol. 1096, No. 4, pp. 345-354(Abstract).

Hoogenboom et al., (1991), "Construction and expression of antibody-tumor necrosis factor fusion proteins," Molecular Immunology, vol. 28, No. 9, pp. 1027-1037.

Huck et al. (1986) "Sequence of a human immunoglobulin gamma 3 heavy chain constant region gene: comparison with the other human Cγ genes," Nucleic Acids Research, vol. 14, No. 4, pp. 1779-1789.

Huse et al. (1989) "Generation of a Large Combinatorial Library of the Immunoglobulin Repertoire in Phage Lambda," Science, vol. 246, pp. 1275-1281.

Ingber et al. (1990) "Synthetic analogues of fumagillin that inhibit angiogenesis and suppress tumour growth," Nature, vol. 348, pp. 555-557.

Jones et al., (1986) "Replacing the complementarity-determining regions in a human antibody with those from a mouse," Nature, vol. 321, No. 6069, pp. 522-525.

Jung et al., (1986), "Activation of human peripheral blood mononuclear cells by anti-T3: Killing of tumor target cells coated with anti-target-anti-T3 conjugates," Proc. Natl. Acad. Sci. USA, vol. 83, pp. 4479-4483.

Junghans et al. (1996) "The protection receptor of IgG catabolism is the B2-micorgobulin-containing neonatal intestinal transport receptor," Proc. Natl. Acad. Sci. USA, vol. 93, No. 11, pp. 5512-5516.

Kang et al., (1991), "Antibody redesign by chain shuffling from random combinatorial immunoglobulin libraries," Proc. Natl. Acad. Sci. USA, vol. 88, pp. 11120-11123.

Kappel, et al. (1992) "Regulating gene expression in transgenic animals," Current Opinion in Biotechnology 3:548-553.

Karpovsky et al., (1984), "Production of Target-Specific Effector Cells using Hetero-Cross Linked Aggregate Containing Anti-Target Cell and AntiFc.lamda. Receptor Antibodies," Journal of Experimental Medicine, vol. 160, No. 6, pp. 1686-1701.

Kendra et al., (1999), "Pharmacokinetics and stability of the ch 14.18-interleukin-2 fusion protein in mice," Cancer Immunol. Immunotherapy, vol. 48, pp. 219-229.

Kim, et al. (1999) "Cytokine Molecular Adjuvants Modulate Immune Responses Induced by DNA Vaccine Constructs for HIV-1 and SIV" Journal of Interferon and Cytokine Research, vol. 19, pp. 77-84.

Kim, et al., (May 1997), "An Ovalbumin-IL-12 fusion protein is more effective than oval bumin plus free recombinant IL-12 in inducing a T helper cell type 1-dominated immune response and inhibiting antigen-specific IgE production." JournalImmunology, vol. 158, No. 9, pp. 4137-4144.

Kranz et al., (1984), "Attachment of an anti-receptor antibody to non-target cells renders them susceptible to lysis by a clone of cytotoxic T lymphocytes", Proc. Natl. Acad. Sci. USA, vol. 81, 7922-7926.

Kuo, et al. (2001) "Oligomerization-dependent Regulation of Motility and Morphogenesis by the Collagen XVIII NC1/Endostatin Domain," Journal of Cell Biology, vol. 152, No. 6, pp. 1233-1246.

LaVallie et al., (1993), "Cloning and Functional Expression of a cDNA Encoding the Catalytic Subunit of Bovine Enterokinase," Journal of Biological Chemistry, vol. 268, No. 31, pp. 23311-23317.

Lazar et al., (1988), "Transforming Growth Factor α: Mutation of Aspartic Acid 47 and Leucine 48 Results in Different Biological Activities," Molecular and Cellular Biology vol. 8, No. 3, pp. 1247-1252.

LeBerthon et al., (1991), "Enhanced Tumor Uptake of Macromolecules Induced by a Novel Vasoactive Interleukin 2 Immunoconjugate," Cancer Research, vol. 51, pp. 2694-2698.

Lieschke, et al., (Jan. 1997), "Bioactive murine and human interleukin-12 fusion proteins which retain antitumor activity in vivo." Nature Biotechnology, vol. 15, No. 1, pp. 35-40.

Linsley et al. (1991) "CTLA-4 is a Second Receptor for B Cell Activation Antigen B7," Journal of Experimental Medicine, vol. 174, No. 3, pp. 561-569.

Liu et al., (1988), "Hormone Conjugated with Antibody to CD3 Mediates Cytotoxic T Cell Lysis of Human Melanoma Cells," Science, vol. 239, pp. 395-398.

Liu et al., (1985), "Heteroantibody Duplexes Target Cells for Lysis by Cytotoxic T Lymphocytes", Proc. Natl. Acad. Sci. USA, vol. 82, pp. 8648-8652.

Lo et al., (1998), "High Level Expression and Secretion of Fc-X Fusion Proteins in Mammalian Cells" Protein Engineering, vol. 11, No. 6, pp. 495-500.

Lode et al., (1998), "Natural Killer Cell-Mediated Eradication of Neuroblastoma Metastases to Bone Marrow by Targeted Interleukin-2 Therapy," Blood, vol. 91, No. 5, pp. 1706-1715.

Lode et al., (1999), "Synergy between an antiangiogenic integrin $\alpha_v$ antagonist and an antibody-cytokine fusion protein eradicates spontaneous tumor metastases," Proc. Natl. Acad. Sci. USA, vol. 96, pp. 1591-1596.

Lode et al., (2000), "Amplification of T Cell Mediated Immune Responses by Antibody-Cytokine Fusion Proteins," Immunological Investigations, vol. 29, No. 2, pp. 117-120.

Lode et al., (1999), "Tumor-targeted IL-2 amplifies T cell-mediated immune response induced by gene therapy with single-chain IL-12," Proc. Natl. Acad. Sci. USA, vol. 96, pp. 8591-8596.

Maloney et al., (1994), "Phase 1 Clinical Trial Using Escalating Single-Dose Infusion of Chimeric Anti-CD20 Monoclonal Antibody (IDEC-C2B8) in Patients with Recurrent B-Cell Lymphoma," Blood, vol. 84, No. 8, pp. 2457-2466.

Martinotti et al., (1995), "CD4 T Cells Inhibit in vivo the CD8-Mediated Immune Response Against Murine Colon Carcinoma Cells Transduced with Interleukin-12 Genes," Eur. J. Immunol. vol. 25, pp. 137-146.

Mark et al., (Dec. 1992), "Expression and characterization of hepatocyte growth factor receptor-IgG fusion proteins." Journal of Biological Chemistry, vol. 267, No. 36, pp. 26166-26171.

Medesan et al. (1997) "Delineation of the Amino Acid Residues Involved in Transcytosis and Catabolism of Mouse IgG1[1]," Journal Immunology, vol. 158, No. 5, pp. 2211-2217.

Mestre et al., (1997), "Retinoids Suppress Epidermal Growth Factor-induced Transcription of cyclooxygenase-2 in Human Oral Squamous Carcinoma Cells," Cancer Research, vol. 57, pp. 2890-2895.

Mosmann et al., (1989), "TH1 and TH2 Cells: Different Patterns of Lymphokine Secretion Lead to Different Functional Properties," Ann. Rev. Immunol. vol. 7, pp. 145-173.

Murphy et al., (1986), "Genetic construction, expression, and melanoma-selective cytotoxicity of a diptheria toxin-related α-melanocyte-stimulating hormone fusion protein," Proc. Natl. Acad. Sci. USA, vol. 83, pp. 8258-8262.

Murphy, (1988), "Diphtheria-related peptide hormone gene fusions: A molecular gene approach t chimeric toxin development," Immunotoxins, pp. 123-140.

Nedwin et al., (1985), "Human Lymphotoxin and Tumor Necrosis Factor Genes: Structure, Homology and Chromosomal Localization," Nucleic Acids Research, vol. 13, No. 17, pp. 6363-6373.

Neuberger, et al., (1984), "Recombinant Antibodies Possessing Novel Effector Functions.," Nature, vol. 312, pp. 604-608.

O'Reilly et al., (1994), "Angiostatin: a Novel Angiogenesis Inhibitor That Mediates the Suppression of Metastases by a Lewis Lung Carcinoma," Cell, vol. 79, pp. 315-328.

O'Reilly et al., (1996), "Angiostatin induces and sustains dormancy of human primary tumors in mice," Nature Medicine, vol. 2, No. 6, pp. 689-692.

O'Reilly et al., (1997), "Endostatin: An Endogenous Inhibitor of Angiogenesis and Tumor Growth," Cell, vol. 88 pp. 277-285.

Pastan et al., (1989), "Pseudomonas Exotoxin: Chimeric Toxins", Journal of Biological Chemistry, vol. 264, No. 26, pp. 15157-15160.

Paul et al., (1988), "Lymphotoxin," Ann. Rev. Immunol., vol. 6, pp. 407-438.

Perez et al., (1986), "Specific Targeting of Human Peripheral Blood T Cells by Heteroaggregates Containing Anti-T3 Crosslinked to Anti-Target cell antibodies," J. Exp. Medicine, vol. 163, pp. 166-178.

Perez et al., (1989), "Isolation and Characterization of a cDNA Encoding the KS1/4 Epithelial Carcinoma Marker," Journal Immunology, vol. 142, No. 10, pp. 3662-3667.

Putzer et al. (1997), "Interleukin 12 and B7-1 Costimulatory Molecule Expressed by an Adenovirus Vector Act Synergistically to Facilitate Tumor Regression," Proc. Nat'l Acad. Sci., vol. 94, pp. 10889-10894.

Reisfeld et al., (1996), "Recombinant antibody fusion proteins for cancer immunotherapy," Current Topics in Microbiology and Immunolgy, pp. 27-53.

Reisfeld et al., (1997), "Immunocytokines: a new approach to immunotherapy of melanoma," Melanoma Research, vol. 7. Suppl. 2, pp. S99-S106.

Riethmuller et al., (1994), "Randomised trial of monoclonal antibody for adjuvant therapy of resected Dukes' C colorectal carcinoma," The Lancet, vol. 343, pp. 1177-1183.

Rosenberg, (1988), "Immunotherapy of Cancer Using Interleukin 2: current status and future prospects," Immunology Today, vol. 9, No. 2, pp. 58-62.

Rozwarski et al., (1994), "Structural comparisons among the short-chain helical cytokines," Structure 2, vol. 2, No. 3, pp. 159-173.

Santon et al., (1986), "Effects of Epidermal Growth Factor Receptor Concentration on Tumorigenicity of A431 Cells in Nude Mice," Cancer Research, vol. 46, pp. 4701-4705.

Sasaki et al., (1998), "Structure, function and tissue forms of the C-terminal globular domain of collagen XVII containing the angiogenesis inhibitor endostatin," the Embo Journal, vol. 17, No. 15, pp. 4249-4256.

Schnee et al., (1987), "Construction and expression of a recombinant antibody-targeted plasminiogen activator," Proc. Natl. Acad. Sci. USA, vol. 84, pp. 6904-6908.

Schoenhaut et al., (1992), "Cloning and Expression of Murine IL-12," Journal of Immunology, vol. 148, No. 11, pp. 3433-3340.

Senter et al., (1988), "Anti-tumor effects of antibody-alkaline phosphatase conjugates in combination with etoposide phosphate," Proc. Natl. Acad. Sci USA, vol. 85, No. 13, pp. 4842-4846.

Shen et al., (1986), "Heteroantibody-Mediated Cytotoxicity: Antibody to the High Affinity Fc Receptor for IgG mediates cytotoxicity by Human Monocytes that is enhanced by interferon γ and is not blocked by human IgG," Journal of Immunology, vol. 137, No. 11, pp. 3378-3382.

Shiff et al., (1995), "Sulindac Sulfide, an Asprin-like Compound, Inhibits Proliferation, Causes Cell Cycle Quiescence, and Induces Apoptosis in HT-29 Colon Adenocarcinoma Cells," Journal of Clinical Investigation, vol. 96, pp. 491-503.

Shin et al., (1990), "Expression and characterization of an antibody binding specificity joined to insulin-like growth factor 1: Potential applications for cellular targeting," Proc. Natl. Acad. Sci. USA, vol. 87, pp. 5322-5326.

Sim et al., (1997), "A Recombinant Human Angiostatin Protein Inhibits Experimental Primary and Metastatic Cancer," Cancer Research, vol. 57, pp. 1329-1334.

Stevenson et al., (1997), "Conjugation of Human Fcγ in Closed-Hinge or Open-Hinge Configuration to Fab'γ and Analogous Ligands," Journal of Immunology, vol. 158, pp. 2242-2250.

Taniguchi et al., (1983), "Structure and expression of a cloned cDNA for human interleukin-2," Nature, vol. 302, pp. 305-309.

Tao et al., (1989), "Studies of Aglycosylated Chimeric Mouse IgG: Role of Carbohydrage in the Structure and Effector Functions Mediated by the Human IgG Constant Region," Journal of Immunology, vol. 143, No. 8, pp. 2595-2601.

Tao et al., (1993), "Structural Features of Human Immunoglobulin G that Determine Isotype-Differences in Copmlement Activation," Journal of Experimental Medicine, vol. 178, No. 2, pp. 661-667.

Teicher et al., (1994), "Potentiation of Cytotoxic Cancer Therapies by TNP-470 Alone and With Other Anti-Angiogenic Agents," Int. J. Cancer, vol. 57, pp. 920-925.

The Merck Manual of Diagnosis and Therapy, 990-993, 1278-1283 (17th ed..1999).

Till et al., (1988), "An Assay that Predicts the Ability of Monoclonal Antibodies to Form Potent Ricin A Chain-containing Immunotoxins," Cancer Research, vol. 48, No. 5, pp. 1119-1123.

Till et al., (1988), "HIV-Infected Cells are Killed by rCD4-Ricin A Chain," Science, vol. 242, pp. 1166-1168.

Trinchieri, (1994), "Interleukin-12: A Cytokine Produced by Antigen-Presenting Cells With Immunoregulatory Functions in the Generation of T-Helper Cells Type 1 and Cytotoxic Lymphocytes," Blood, vol. 84, pp. 4008-4027.

Vagliani et al., (1996), "Interleukin 12 Potentiates the Curative Effect of a Vaccine Based on Interleukin 2-transduced Tumor Cells," Cancer Research, vol. 56, pp. 467-470.

Varki et al., (1984), "Antigens Associated with a human lung adenocarcinoma defined by monoclonal antibodies," Cancer Research, vol. 44, pp. 681-687.

Verhoeyen et al.(1988) "Reshaping Human Antibodies: Grafting an Antilysozyme Activity," Science 239:1534-1536.

Williams et al., (1987), "Diphtheria toxin receptor binding domain substitution with interleukin-2: genetic construction and properties of a diphtheria toxin-related interleukin-2 fusion protein", Protein Engineering, vol. 1, No. 6, pp. 493-498.

Williams et al., (1986), "Production of antibody-tagged enzymes by myeloma cells: application to DNA polymerase 1 Klenow fragment," Gene, vol. 43, pp. 319-324.

Wooley et al. (1993) "Influence of a Recombinant Human Soluble Tumor Necrosis Factor Receptor FC Fusion Protein on Type II Collagen-Induced Arthritis in Mice," J. Immunol. 151: 6602-6607.

Wu et al.,( Jul. 1997), "Suppression of Tumor Growth with Recombinant Murine Angiostatin", Biochemical and Biophysical Research Communications, vol. 236, No. 3, pp. 651-654.

Xiang et al.(1997) "Elimination of Established Murine Colon Carcinoma Metastases by Antibody-Interleukin 2 Fusion Protein Therapy," Cancer Research, vol. 57, pp. 4948-4955.

Zheng, et al., (1995), "Administration of nonstyolytic IL-10/Fc in murine models of lipopolysaccaride-induced septic shock and allogenic islet transplantation." Journal Immunology, vol. 154, No. 10, pp. 5590-5600.

Afonso et al., (1994), "The Adjuvant Effect of Interleukin-12 in a Vaccine Against Leishmania Major," Science, 263:235-237.

Becker et al., (1996), "An Antibody-Interleukin 2 Fusion Protein Overcomes Tumor Heterogeneity by Induction of a Cellular Immune Response," Proc. Natl. Acad. Sci., 93:7826-7831.

Beutler et al., (1988), "Tumor Necrosis, Cachexia, Shock, and Inflammation: A Common Mediator," Ann. Rev. Biochem., 57:505-518.

Bissery et al., (1997), Cancer Therapeutics: Experimental and Clinical Agents, Teicher Edition, Ch. 8.

Buchli et al., (1993), "Structural and Biologic Properties of a Human Aspartic Acid-126 Interleukin-2 Analog," Archives of Biochemistry and Biophysics, 307:2:411-415.

Caton et al., (1986), "Structural and functional implications of a restricted antibody response to a defined antigenic region on the influenza virus hemagglutinin," The EMBO Journal, 5:7:1577:1587.

Chang et al., (1996), "A Point Mutation in Interleukin-2 that Alters Ligand Internalization," Journal of Biological Chemistry, 271:23:13349-13355.

Chuang et al., (1993), "Effect of new investigational drug taxol on oncolytic activity and stimulation of human lymphocytes," Gynecol. Oncol., 49:291-298.

Collins et al., (1988), "Identification of Specific Residues of Human Interleukin 2 that Affect Binding to the 70-kDa Subunit (p70) of the Interleukin 2 Receptor," Proc. Natl. Acad. Sci, 85:7709-7713.

Fell et al., (1992), "Chimeric L6 antitumor antibody," The J. of Biol. Chem., 267:22:15552-15558.

Griffon-Etienne et al., (1999), "Taxane-induced apoptosis decompresses blood vessels and lowers interstitial fluid pressure in solid tumors: clinical implications," Cancer Research, 59:3776-3782.

Heijnen et al., (1996), "Antigen Targeting to Myeloid-specific Human FcγRI/CD64 Triggers Enhanced Antibody Responses in Transgenic Mice," J. Clin. Invest., 97:2:331-338.

Hornick et al., (1999), "Pretreatment with a monoclonal antibody/interleukin-2 fusion protein directed against DNA enhances the delivery of therapeutic molecules to solid tumors," Clin. Cancer Res., 5:51-60.

Hu et al., (1996), "A chimeric Lym-1/Interleukin 2 Fusion Protein for Increasing Tumor Vascular Permeability and Enhancing Antibody Uptake," Cancer Research, 56:4998-5004.

Ju et al., (1987), "Structure-Function Analysis of Human Interleukin-2," Journal of Biological Chemistry, 262:12:5723-5731.

Liu et al., (1998), "Immunostimulatory CpG Oligodeoxynucleotides Enhance the Immune Response to Vaccine Strategies Involving Granulocyte-Macrophage Colony-Stimulating Factor," Blood, 92:3730-3736.

Lode et al., (1998), "Immunocytokines: a promising approach to cancer immunotherapy," Pharmcol. Thera., 80:277-292.

Mott et al., (1995), "The Solution Structure of the F42A Mutant of Human Interleukin 2," J. Mol. Biol., 247:979-994.

Mullins et al., (1998), "Interleukin-12 overcomes paclitaxel-mediated suppression of T-cell proliferation," Immunopharmacol. Immunotoxicol., 20:473-492.

Netti et al., (1995), "Time-dependent behavior of interstitial fluid pressure in solid tumors: implications for drug delivery," Cancer Research, 55:5451-5458.

Netti et al., (1999), "Enhancement of fluid filtration across tumor vessels: implication for delivery of macromolecules," Proc. Nat. Acad. Sci., 96:3137-3142.

Polizzi et al., (1999), "A novel taxane with improved tolerability and therapeutic activity in a panel of human tumor xenografts," Cancer Res., 59:1036-1040.

Roessler et al., (1994), "Cooperative Interactions between the interleukin 2 receptor α and β chains alter the interleukin 2-bindign affinity of the receptor subunits," Proc. Natl. Acad. Sci., 91:3344-3347.

Roitt et al., (1993), "The Role of TH Cells in the Selection of Effector Mechanisms Directed Against Target Antigens," Immunology, Third Edition, 8.3-8.4.

Sauve et al., (1991), "Localization in human interleukin 2 of the binding site of the α chain (p55) of the interleukin 2 receptor," Proc. Natl. Acad. Sci., 88:4636-4640.

Shanafelt et al., (2000), "A T-cell-selective interleukin 2 mutein exhibits potent antitumor activity and is well tolerated in vivo," Nature Biotechnology, 18:1197-1202.

Sharma et al., (1999), "T cell-derived IL-10 promotes lung cancer growth by suppressing both T cell and APC function," J. Immunol., 163:50520-5028.

Sulitzeanu et al., (1993), "Immunosuppressive factors in human cancer," Adv. Cancer Res., 60:247-267.

Villunger et al., (1997), "Constitutive expression of Fas (Apo-1/CD95) ligand on multiple myeloma cells: a potential mechanism of tumor-induced suppression of immune surveillance," Blood, 90:12-20.

Watanabe et al., (1997), "Long-term depletion of naive T cells in patients treated for Hodgkin's disease," Blood, 90:3662-3672.

Angal et al., (1993), "A Single Amino Acid Substitution Abolishes the Heterogeneity of Chimeric Mouse/Human (IgG4) Antibody," Molecular Immunology, 30(1):105-108.

Batra et al., (1993), "Insertion of Constant Region Domains of Human IgG1 into CD4-PE40 Increases Its Plasma Half-Life," Mol. Immunol., 30(4):379-386.

Becker et al., (1996), "Long-lived and Transferable Tumor Immunity in Mice after Targeted Interleukin-2 Therapy," J Clin Invest., 98(12):2801-2804.

Becker et al., (1996), "T Cell-mediated Eradication of Murine Metastatic Melanoma Induced by Targeted Interleukin-2 Therapy," J Exp. Med., 183(50):2361-6.

Bitonti et al., (2002), "Transepithelial Absorption of an Erythropoietin-Fc Fusion Protein After Delivery to the Central Airways," Respiratory Drug Delivery, 8:309-312.

Boissel et al., (1993), "Erythropoietin Structure-Function Relationships: Mutant Proteins that Test a Model of Tertiary Structure," The Journal of Biological Chemistry, 268(21):15883-15993.

Briggs et al., (1974), "Hepative Clearance of Intact and desialylated Erythropoietin," American Journal of Physiology, 227(6):1385-1388.

Chuang et al., (1994), "Alteration of Lymphocyte Microtubule Assembly, Cytotoxicity, and Activation by the Anticancer Drug Taxol," Cancer Research, 54:1286-1291.

Cruse et al., (1995), Illustrated Dictionary of Immunology, CRC Press, NY, p. 156-7.

Darling et al., (2002), "Glycosylation of Erythropoietin Affects Receptor Binding Kinetics: Role of Electrostatic Interactions," Biochemistry, 41 :14524-14531.

Davis et al., (2003), "Immunocytokines: Amplification of Anti-cancer Immunity," Cancer Immunol. Immunother., 52:297-308.

Dolman et al., (1998), "Suppression of Human Prostate Carcinoma Metastases in Severe Combined Immunodeficient Mice by Interleukin 2 Immunocytokine Therapy," Clin Cancer Res., 4(10):2551-7.

Duncan et al., (1988), "The Binding Site for C1q on IgG," Nature, 332:738-740.

Egrie et al., (2001), "Development and Characterization of Novel Erythropoiesis Stimulating Protein (NESP)," Nephrol. Dial. Transplant., 16:3-13.

Elliott et al., (1997), "Mapping of the Active Site of Recombinant Human Erythropoietin," Blood, 89(2):493-502.

Fibi et al., (1995), "N- and O-Glycosylation Muteins of Recombinant Human Erythropoietin Secreted From BHK-21 Cells," Blood, 85(5):1229-1236.

Frost et al., (1997), "A Phase I/IB Trial of Murine Monoclonal Anti GD2 Antibody 14.G2a Plus Interleukin-2 in Children with Refractory Neuroblastoma," Cancer, 80:317-33.

Gan et al., (1999), "Specific enzyme-linked Immunosorbent Assays for Quantitation of Antibody-cytokine Fusion Proteins," Clin. Diagn. Lab. Immunol., 6(2):236-42.

Gillies et al., (1991), "Expression of Genetically Engineered Immunoconjugates of Lymphotoxin and a Chimeric Anti-ganglioside GD2 Antibody," Hybridoma., 10(3):347-56.

Gillies et al., (2002), "Bi-functional Cytokine Fusion Proteins for Gene Therapy and Antibody-targeted Treatment of Cancer," Cancer Immunol. Immunother., 51(8):449-60.

Gillies et al., (2002), "Improved Circulating Half-life and Efficacy of an Antibody-interleukin 2 Immunocytokine Based on Reduced Intracellular Proteolysis," Clin. Cancer Res., 8(1):210-6.

Greene et al., (1975), Neuronal Properties of Hybrid Neuroblastoma X Sympathetic Ganglion Cells, Proc. Natl. Acad. Sci. USA, 72(12):4923-4927.

Hammerling et al. (1996), "In Vitro Bioassay for Human Erythropoietin based on Proliferative Stimulation of an Erythroid Cell Line and Analysis of Carbohydrate-dependent Microheterogeneity," Journal of Pharmaceutical and Biomedical Analysis,14:1455-1469.

Hank et al., (1996), "Activation of Human Effector Cells by a Tumor Reactive Recombinant Anti-ganglioside GD2 Interleukin-2 Fusion Protein (ch14.8-IL2)," Clin Cancer Res., 2(12):1951-9.

Hank et al., (2003), "Determination of peak serum levels and immune response to the humanized anti-ganglioside antibody-interleukin-2 immunocytokine," Methods Mol. Med., 85:123-31.

Haraguchi, (1994), "Isolation of GD3 Synthase Gene by Expression Cloning of GM3 α-2,8-sialytrasnferase Cdna using anti-GD2 Monoclonal Antibody," Proc. Natl. Acad. Sci. USA., 91 (22):10455-9.

Harris, (1995), "Processing of C-terminal Lysine and Arginine Residues of Proteins Isolated from Mammalian Cell Culture," J. Chromatogr. A., 705:129-134.

Harvill et al., (1995), "A IgG3-IL2 Fusion Protein Activates Complement, Binds FcYRI, Generates LAK Activity and Shows Enhanced Binding to the High Affinity IL-2R," Immunotech., 1:95-105.

Hezareh et al, (2001), "Effector Function Activities of a Panel of Mutants of a Broadly Neutralizing Antibody against Human Immunodeficiency Virus Type 1," J. Virol., 75(24):12161-8.

Idusogie et al., (2000), "Mapping of the C1q Binding Site of Rituxan, a Chimeric Antibody with a Human IgG1 Fc," J. Immunol., 164(8):4178-4184.

Imboden et al., (2001), "The Level of MHC Class I Expression of Murine Adenocarcinoma Can Change the Antitumor Effector Mechanism of Immunocytokine Therapy," Cancer Res., 61(4):1500-7.

Kato et al., (1997), "Mechanism for the Nonlinear Pharmacokinetics of Erythropoietin in Rats," The Journal of Pharmacology and Experimental Therapeutics, 283:520-527.

Kato et al., (1998), "Pharmacokinetics of Erythopoietin in Genetically Anemic Mice," Drug Metabolism and Disposition, 26:126-131.

Kitamura et al. (1989), "Establishment and Characterization of a Unique Human Cell Line that Proliferates Dependently on GM-CSF, IL-3, or Erythropoietin," Journal of Cellular Physiology, 140:323-334.

Kushner et al., (2001), "Phase II Trial of the Anti-GD2 Monoclonal-macrophage-colony-stimulating Factor for Neuroblastoma," J. Clin. Oncol., 19:4189-94.

Locatelli et al., (2001), "Darbepoetin alfa Amgen," Current Opinion in Investigational Drugs, 2:1097-1104.

Lode et al., (2000), "What to do with Targeted IL-2," Drugs Today, 36(5):321-36.

Lode et al., (2000), "Melanoma Immunotherapy by Targeted II-2 Depends on CD4(+) T-cell Help Mediated by CD40/CD4OL Interaction," J. Clin. Invest., 105(11):1623-30.

Macdougall, (2002), "Optimizing the Use of Erythropoietic Agents—Pharmacokinetic and Pharmacodynamic Considerations," Nephrol. Dial. Transplant., 17:66-70.

Metelitsa et al., (2002), "Antidisialoganglioside/granulocyte Macrophage-colony-stimulating Factor Fusion Protein Facilitates Neutrophil Antibody-dependent Cellular Cytotoxicity and Depends on FcγRII (CD32) and Mac-1 (CD11b/CD18) for EnhancedEffector Cell Adhesion and Azurophil Granule Exocytosis," Blood, 99(11):4166-73.

Mueller et al. (1997), "Humanized Porcine VCAM-specific Monoclonal Antibodies with Chimeric IgG2/G4 Constant Regions Block Human Leukocyte Binding to Porcine Endothelial Cells," Molecular Immunology, 34(6):441-452.

Mullins et al. (1997), "Taxol-mediated Changes in Fibrosarcoma-induced Immune Cell Function: Modulation of Antitumor Activities," Cancer Immunol. Immunother, 45:20-28.

Naramura et al., "Mechanisms of Cellular Cytotoxicity Mediated by a Recombinant Antibody-IL2 Fusion Protein against Human Melanoma Cells," Immunology Letters, 39(1):91-9, (2003 ).

Neal et al. (2003), "NXS2 Murine Neuroblastomas Express Increased Levels of MHC Class I Antigens upon Recurrence Following NK-dependent Immunotherapy," Cancer Immunol Immunother., 53:41-52.

Ngo et al., (1994), "The Protein Folding Problem and Tertiary Structure Prediction," pp. 433-440 and 492-495, Birkhauser Boston.

Niethammer et al., (2002) "An oral DNA Vaccine against Human Carcinembryonic Antigen (CEA) Prevents Growth and Dissemination of Lewis Lung Carcinoma in CEA Transgenic Mice," Vaccine, 20:421-9.

Neithammer et al., (2001) "Targeted Interleukin 2 Therapy Enhances Protective Immunity Induced by an Autologous Murine Melanoma," Cancer Res., 61(16):6178-84.

Nimtz et al., (1993) Structures of Sialylated Oligosaccharides of Human Erythropoietin Expressed in Recombinant BHK-21 Cells, Eur. J. Biochem., 213:39-56.

Pancook et al., (1996), "Eradication of Established Hepatic Human Neuroblastoma Metastases in Mice with Severe Combined Immunodeficiency by Antibody-targeted Interleukin-2," Cancer Immunol. Immunother., 42(2):88-92.

Park et al., (2000), "Efficiency of Promoter and Cell line in High-level Expression of Erythropoietin," Biotechnol. Appl. Biochem., 32:167-172.

Reisfeld et al., (1996), "Antibody-interleukin 2 Fusion Proteins: A New Approach to Cancer Therapy," J Clin Lab Anal., 10(3)1 60-6.

Reisfeld et al., (1996), "Involvement of B Lymphocytes in the Growth Inhibition of Human Pulmonary Melanoma Mestastases in Athymic nu/nu Mice by an Antibody-lymphotoxin Fusion Protein," Cancer Res., 56(8):1707-12.

Ruehlmann et al., (2001), "MIG (CIXCL9) Chemokine Gene Therapy Combines with Antibody-cytokine Fusion Protein to Ssuppress Growth and Dissemination of Murine Colon Carcinoma," Cancer Res., 61(23):8498-503.

Sabzevari et al., (1994), "A Recombinant Antibody-interleukin 2 Fusion Protein Suppresses Growth of Hepatic Human Severe Combined Immunodeficiency Mice," Proc. Natl. Acad. Sci. USA, 91(20):9626-30.

Seidenfeld et al., (2001), "Epoietin Treatment of Anemia Associated with Cancer Therapy: A Systematic Review and Meta-analysis of controlled Clinical Trials," Journal of National Cancer Institute, 93:1204-1214.

Shinkawa et al., (2003), "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," J. Biol. Chem., 278:3466-3473.

Spiekermann et al., (2002), "Receptor-mediated Immunoglobulin G Transport Across Mucosal Barriers in Adult Life: Functional Expression of FcRn in the Mammalian Lung," J. Exp. Med., 196:303-310.

Strom et al., (1996), "Therapeutic Approach to Organ Transplantation," Therapeutic Immunology, Blackwell Science, Chapter 36, pp. 451-456.

Syed et al., (1998), "Efficiency of Signaling through Cytokine Receptors Depends Critically on Receptor Orientation," Nature, 395:511-516.

Thommesen et al., (2000), "Lysine 322 in the Human IgG3 CH2 Domain is Crucial for Antibody Dependent Complement Activation," Mol. Immunol., 37(16):995-1004.

Wells, (1990), "Additivity of Mutational Effect in Proteins," Biochemistry, 29(37):8509-8517.

Wen et al., (1993), "Erythropoietin Structure-Function Relationships: High Degree of Sequence Homology Among Mammals," Blood, 82(5):1507-1516.

Xiang et al., (1998), "Induction of Persistent Tumor-protective Immunity in Mice Cured of Established Colon Carcinoma Metastases," Cancer Research, 58(17)3918-3925.

Xiang et al., (1999) "T Cell Memory against Colon Carcinoma is Long-lived in the Absense of Antigen," J. Immunol., 163(7):3676-83.

Xiang et al., (2001), "A Dual Function DNA Vaccine Encoding Carcinoembryonic Antigen and CD40 Ligand Trimer induces T Cell-mediated Protective Immunity Against Colon Cancer in Carcinoembryonic Antigen-Transgenic Mice," J Immunol., 167(8):4560-5.

Xiang et al., (2001), "Protective Immunity Against Human Carcinoembryonic Antigen (CEA) Induced by an Oral DNA Vaccine in CEA-transgenic Mice," Clin Cancer Res., 7(3 Supp):S856-S864.

Xu et al., (1994), "Residue at Position 331 in the IgG1 and IgG4 CH2 Domains Contributes to Their Differential Ability to Bind and Activate Complement," J. Biol. Chem., 269(5):3469-3474.

Yu et al., (1998), "Phase 1 Trial of a Human-Mouse Chimeric Anti-Disaloganglioside Monoclonal Antibody ch14.18 in Patients with Refractory Neuroblastoma and Osteosarcoma," J. Clin. Oncol., 16(6):2169-80.

Zagozdzon et al. (1999), "Potentiation of Antitumor Effect of IL-12 in Combination with Paclitaxel in Murine Melanoma Model In Vivo," International Journal of Molecular Medicine, 4:645-648.

de la Salle et al., (1996), "FcγR on Human Dendritic Cells," in Human IgG Receptors, pp. 39-55, van de Winkel et al. (eds.), R.G. Landes Co.

Elliott et al., (1996), "Fine-Structure Epitope Mapping of Antierythropoietin Monoclonal Antibodies Reveals a Model of Recombinant Human Erythropoietin Structure," Blood, 87(7):2702-2713.

Hurn et al., (1980), "Production of Reagent Antibodies," Methods in Enzymology, 70: 104-142.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," J. Immunology, 114(6):1726-1729.

Lode et al., (1997), "Targeted Interleukin-2 Therapy for Spontaneous Neuroblastoma Metastases to Bone Marrow," J. Natl. Cancer Inst., 89(21):1586-94.

Sallusto et al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," J. Exp.Med., 179:1109-1118.

Schlom (1991), "Monoclonal Antibodies: They're More and Less Than You Think," in Molecular Foundations of Oncology, pp. 95-133.

Wen et al., (1994), "Erythropoietin Structure-Function Relationships: Identification of Functionally Important Domains," J. Biological Chemistry, 269(36):22839-22846.

International Search Report for International Patent Application Serial No. PCT/US98/25978, dated Jun. 18, 1999.

Maecker et al., (1997), "DNA Vaccination with Cytokine Fusion Constructs Biases the Immune Response to Ovalbumin," Vaccine, 15(15):1687-1698.

Chapman et al., (1994), "Mapping Effector Functions of a Monoclonal Antibody to GD3 by Characterization of a Mouse-Human Chimeric Antibody," Cancer Immuno. Immunother., 39:198-204.

Conner et al., (2004), "Ex vivo Evaluation of Anti-EpCAM Immunocytokine huKS-IL2 in Ovarian Cancer," J. Immunotherapy, 27:211-219.

Dorai et al., (1991), "Aglycosylated Chimeric Mouse/Human IgG1 Antibody Retains Some Effector Function," Hybridoma, 10(2):211-217.

Dorai et al., (1992), "Role of Inter-Heavy and Light Chain Disulfide Bonds in the Effector Functions of Human IgG1," Molecular Immunology, 29(12):1487-1491.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," J. Immunology, 146(3):1067-1071.

Handgretinger et al., (1995), "A Phase I Study of Human/Mouse Chimeric Anti-ganglioside GD2 Antibody ch14.18 in Patients with Neuroblastoma," European J. Cancer, 31A(2):261-267.

Ko et al., (2004), "Safety, Pharmcokinetics, and Biological Pharmacodynamics of the Immunocytokine EMD 273066 (huKS-IL2)," J. Immunotherapy, 27:232-239.

Lo et al., (1992), "Expression and Secretion of an Assembled Tetrameric CH2-deleted Antibody in E. coli.," Hum. Antibod. Hybridomas, 3:123-128.

Mueller et al., (1990), "Enhancement of Antibody-Dependent Cytotoxicity With A Chimeric Anti-GD2 Antibody," J. Immunology, 144(4):1382-1386.

Mueller et al., (1990), "Serum Half-Life and Tumor Localization of a Chimeric Antibody Deleted of the CH2 Domain and Directed Against the Disialoganglioside GD2," Proc. Natl. Acad. Sci. USA., 87:5702-5705.

Naramura et al., (1993), "Therapeutic Potential of Chimeric and Murine Anti-(Epidermal Growth Factor Receptor) Antibodies in a Metastasis Model for Human Melanoma," Cancer Immuno. Immunother., 37:343-349.

Pertl et al., (2003), "Immunotherapy with a Posttranscriptionally Modified DNA Vaccine Induces Complete Protection Against Metastatic Neuroblastoma," Blood, 101(2):649-654.

Reisfeld et al., (1994), "Potential of Genetically Engineered Anti-Ganglioside GD2 Antibodies for Cancer Immunotherapy," Prog. Brain Res., 101:201-212.

Saleh et al., (1992), "Phase 1 Trial of the Chimeric Anti-GD2 Monoclonal Antibody ch14.18 in Patients With Malignant Melanoma," Hum. Antiob. Hybridomas, 3:19-24.

Weber et al., (2001), "Phase 1 Trial of huKS-IL2 Immunocytokine in Patients with Prostate Carcinoma: Clinical, PK, and Biological PD Results (Abstract)," American Society of Clinical Oncology Program/Proceedings, 20(Part 1):259a.

Boulianne et al., (1984), "Production of Functional Chimaeric Mouse/Human Antibody," Nature, 312:643-6.

Bubenik et al., (1995), "Interleukin-2 Gene Therapy of Residual EL-4 Leukaemia Potentiates the Effect of Cyclophosphamide Pretreatment," J. Cancer Res. Clin. Oncol., 121:39-43.

Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," J. Immunol., 148:92-98.

Desai et al., (1992), "IL-12 Receptor. II. Distribution and Regulation of Receptor Expression," J. Immunol., 148:3125-32.

Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," J. Clin. Invest., 82:1956-1962.

Huston et al., (1988), "Protein Engineering of Antibody Binding Sites: Recovery of Specific Activity in an Anti-Digoxin Single-Chain Fv Analogue Produced in *Escherichia coli*," Proc. Natl. Acad. Sci. USA, 85:5879-5883.

Lanza et al., (1993), "Active Immunity against the CD4 Receptor by Using an Antibody Antigenized with Residues 41-55 of the First Extracellular Domain," Proc. Natl. Acad. Sci. USA, 90:11683-7.

Lode et al., (1998), "Gene Therapy with a Single Chain Interleukin 12 Fusion Protein Induces T Cell-Dependent Protective Immunity in a Syngeneic Model of Murine Neuroblastoma," Proc. Natl. Acad. Sci. USA, 95:2475-80.

Lotze et al., (1996), "Cytokine Gene Therapy of Cancer Using Interleukin-12: Murine and Clinical Trials," Ann. NY Acad. Sci., 795:440-54.

MacLean et al., (1996), "Enhancing the Effect of Theratope STn-KLH Cancer Vaccine in Patients with Metastatic Breast Cancer by Pretreatment with Low-Dose Intravenous Cyclophosphamide," J. Immunother., 19(4):309-316.

Maghazachi et al., (1997), "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," FASEB J., 11:765-74.

Mariani et al., (1997), "Tumor Targeting Potential of the Monoclonal Antibody BC-1 against Oncofetal Fibronectin in Nude Mice Bearing Human Tumor Implants," Cancer, 80:2378-84.

McMahan et al., (1991), "A Novel IL-1 Receptor, Cloned From B-Cells by Mammalian Expression is Expressed in Many Cell Types," EMBO J., 10:2821-32.

Mehrotra et al., (1993), "Effects of IL-12 on the Generation of Cytotoxic Activity in Human CD8+ T Lymphocytes," J. Immunol., 151:2444-52.

Menard et al., (1983), "Generation of Monoclonal Antibodies Reacting with Normal and Cancer Cells of Human Breast," Cancer Res., 43:1295-300.

Miyake et al., (1988), "Synthesis of Recombinant Human Single-Chain Urokinase-Type Plasminogen Activator Variants Resistant to Plasmin and Thrombin," J. Biochem., 104:643-647.

Nastala et al., (1994), "Recombinant IL-12 Administration Induces Tumor Regression in Association with IFN-γ Production," J. Immunol., 153:1697-706.

Nelles et al., (1987), "Characterization of Recombinant Human Single Chain Urokinase-Type Plaminogen Activtor Mutants Produced by Site-Specific Mutagenesis of Lysine 158," J. Biol. Chem., 262(12):5682-5689.

Ngo et al., (1994), "Computational Complexity, Protein Structure Prediction, and the Levinthal Paradox," in The Protein Folding Problem and Tertiary Structure Prediction, Merz et al. (eds.), pp. 433-440 and 492-495, Birkhauser, Boston, MA.

Orlandi et al., (1989), "Cloning Immunoglobulin Variable Domains for Expression by the Polymerase Chain Reaction," Proc. Natl. Acad. Sci. USA, 86:3833-7.

Perussia et al., (1992), "Natural Killer (NK) Cell Stimulatory Factor of IL-12 Has Differential Effects of the Proliferation of TCR-αβ+, TCR-γδ+ T Lymphocytes, and NK Cells," J. Immunol., 149:3495-502.

Queen et al., (1989), "A Humanized Antibody that Binds to the Interleukin 2 Receptor," Proc. Natl. Acad. Sci. USA, 86:10029-33.

Ricchmann et al., (1988), "Reshaping Human Antibodies for Therapy," Nature, 332:323-7.

Robinson et al., (1998), "Optimizing the Stability of Single-Chain Proteins by Linker Length and Composition Mutagenesis," Proc. Natl. Acad. Sci. USA, 95:5929-34.

Sharp et al., (1988), "Codon Usage Patterns in *Escherichia coli, Bacillus subtilis, Saccharomyces cerevisiae, Shizosaccharomyces pombe, Drosophila melanogaster* and *Homo sapiens*; a Review of the Considerable Within-Species Diversity," Nucleic AcidsRes., 16(17):8207-8211.

Tiruppathi et al., (1996), "Isolation and Characterization of a Cell Surface Albumin-Binding Protein from Vascular Endothelial Cells," Proc. Nat. Acad. Sci. USA, 93:250-4.

Voest et al., (1995), "Inhibition of Angiogenesis in Vivo by Interleukin 12," J. Natl. Canc. Inst., 87:581-6.

Weitkamp et al., (1973), "Additional Data on the Population Distribution of Human Serum Albumin Genes; Three New Variants," Ann. Hum. Genet., 37:219-26.

Wysocka et al., (1995), "Interleukin-12 is Required for Interferon-γ Production and Lethality in Lipopolysaccharide-Induced Shock in Mice," Eur. J. Immunol., 25:672-6.

Yan et al., (1996), "Characterization of an Ig VH Idiotope that Results in Specific Homophilic Binding and Increased Avidity for Antigen," J. Immunol., 157:1582-8.

Yeh et al., (1992), "Design of Yeast-Secreted Albumin Derivatives for Human Therapy: Biological and Antiviral Properties of a Serum Albumin-CD4 Genetic Conjugate," Proc. Natl. Acad. Sci. USA, 89:1904-8.

* cited by examiner p35    p40 p35   p40

Fc    Fc-dimer

Fc-p35 (NOT SECRETED)

Fc-p40 (SECRETED)

Fc-p35/Fc-p40 (SECRETED)

Fc-p35/p40 (SECRETED)

Fc-p40/p35 (SECRETED)

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
ccagaaagca agagaccaga g                                             21

<210> SEQ ID NO 2
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 2
ggagggacct cgagttttag gaagcattca g                                  31

<210> SEQ ID NO 3
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 3
ctccgtcctg tctagagcaa gatgtgtc                                      28

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 4
gcttctcgag aacctaactg cagggcacag                                    30
```

```
<210> SEQ ID NO 5
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 5
cctctactaa catgtgtcaa tcacgctacc tc                                    32

<210> SEQ ID NO 6
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 6
ccctcgagtc aggcggagct cagatagcc                                        29

<210> SEQ ID NO 7
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 7
ccgggcaagt cca                                                         13

<210> SEQ ID NO 8
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 8
tatggacttg c                                                           11

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
ccgggaagaa acctccccgt gg                                               22

<210> SEQ ID NO 10
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 10
ccacggggag gtttcttc                                                    18
```

HETERODIMERIC FUSION PROTEINS USEFUL FOR TARGETED IMMUNE THERAPY AND GENERAL IMMUNE STIMULATION

CROSS REFERENCE TO RELATED APPLICATIONS

This application is a division of U.S. patent application Ser. No. 11/804,895, filed May 21, 2007, issued as U.S. Pat. No. 7,576,193 on Aug. 18, 2009, which is a continuation of U.S. patent application Ser. No. 10/935,532, filed Sep. 7, 2004, issued as U.S. Pat. No. 7,226,998 on Jun. 5, 2007, which is a continuation of U.S. patent application Ser. No. 10/005,212, filed Dec. 4, 2001, issued as U.S. Pat. No. 6,838,260 on Jan. 4, 2005, which is a continuation of U.S. patent application Ser. No. 08/986,997, filed Dec. 8, 1997, now abandoned, the contents of each of which are incorporated by reference herein.

FIELD OF THE INVENTION

The present invention relates generally to fusion proteins. More specifically, the present invention relates to heterodimeric fusion proteins useful for targeted immune therapy and general immune stimulation.

BACKGROUND OF THE INVENTION

One of the key immune regulators is the T helper cell which reacts to antigens presented on HLA class II molecules. This CD4+ cell differentiates in response to antigenic stimulation and becomes a type 1 or type 2 helper (Th1 or Th2) according to the type of cytokines that it secretes. Mosmann and Coffman. *Ann. Rev. Immunol.* 7:145-173 (1989). A Th1 response leads to the secretion of interleukin-2 (IL-2) and interferon-γ (IFN-γ) which stimulates cell-mediated immune reactions against intracellular pathogens. A Th2 response leads to the secretion of IL-4, IL-5 and IL-10 which stimulates antibody responses to extracellular pathogens. The most interesting component of this system of regulation is that one response inhibits the other through the negative regulator activities of the cytokines that are produced. Thus, IL-4 and IL-10 can down-regulate Th1 responses while IFN-γ can down-regulate Th2 responses.

The regulatory activity of T helper cells and their differentiation following exposure to antigen is regulated by cytokines as well. IL-12, a disulfide-linked heterodimeric cytokine with a 40 kDa subunit and 35 kDa subunit, exerts a powerful positive regulatory influence on the development of Th1 helper T-cell immune responses. See review by Trinchieri, *Blood* 84: 4008-4027 (1994). IL-12 also has a powerful synergistic effect in the induction of IFN-γ from both T helpers and natural killer (NK) cells (Eur. Patent Appl. 90123670.3). Secreted IFN-γ then inhibits any Th2 cell proliferation and polarizes the response to favor cell-mediated immunity.

One way of changing the outcome of an immune response would be to administer the appropriate cytokine at the time of antigen stimulation. If IL-4 was the major cytokine present during antigen stimulation, the Th2 response would be enhanced and the Th1 response would be inhibited. In contrast, if IL-12 was the major cytokine present during antigen stimulation, the Th1 response would be enhanced and the Th2 response would be inhibited. However, systemic administration of cytokines is difficult due to their very short circulating half-lives and their deleterious side effects.

A better approach is to target the effect of the cytokine to a cell surface antigen by fusing it to an antibody (or fragment derived therefrom) having specificity and affinity for that antigen. See Gillies, et al., *Proc. Natl. Acad. Sci.* 89: 1428-1432 (1992); U.S. Pat. No. 5,650,150, the disclosure of which is incorporated herein by reference. Alternatively, the stimulatory cytokine can be linked to a protein antigen via a peptide linkage in the form of a fusion protein. See Hazama, et al., *Vaccine* 11: 629-636 (1993). However, the complex structure of IL-12 makes it more difficult to express as a fusion protein due to the necessity of expressing exactly the same molar ratio of each subunit in the final product. In fact, IL-12 itself is naturally expressed and secreted as a mixture of p40 homodimer. D'Andrea, et al., *J. Exp. Med.,* 176: 1387-1398 (1992).

Therefore, there is a need in the art for methods of producing fusion proteins with heterodimeric cytokines and an antibody or an antigen that maintain the natural heterodimeric structure of the cytokine and secretes the molecules with equimolar ratios of the subunits.

SUMMARY OF THE INVENTION

The present invention provides heterodimeric fusion proteins useful for targeted immune therapy and general immune stimulation and methods for producing these heterodimeric fusion proteins. Specifically, the present invention provides methods for the production of fusion proteins with IL-12 that maintain its natural heterodimeric structure, and provide for the secretion of the molecules with equimolar ratios of IL-12 subunits.

In one aspect of the invention, the fusion proteins comprise a heterodimeric cytokine linked to an antibody, or a portion thereof. In a preferred embodiment, the fusion protein comprises two chimeric chains linked by a disulfide bond. Each chimeric chain comprises a different subunit of the heterodimeric cytokine linked through a peptide bond to a portion of an Ig heavy chain.

In an alternative preferred embodiment, the fusion protein comprises a first chimeric chain comprising one of the subunits of the heterodimeric cytokine linked by a peptide bond to a portion of an Ig heavy chain. This subunit is linked by a disulfide bond to the other subunit of the heterodimeric cytokine. In another alternative preferred embodiment, this first chimeric chain is linked by a disulfide bond to a second chimeric chain comprising one of the subunits of the heterodimeric cytokine linked by a peptide bond to a portion of an Ig heavy chain and by a disulfide bond to the other subunit of the heterodimeric cytokine.

In yet another alternative preferred embodiment, the fusion protein is a trimeric fusion protein comprising a first and a second chimeric chain linked by a disulfide bond. Each chimeric chain comprises a subunit of the heterodimeric cytokine linked by a peptide bond to a portion of an Ig heavy chain. The subunit of one of the chimeric chains is further linked by a disulfide bond to a different subunit of the heterodimeric cytokine.

Fusion proteins of the invention may be considered chimeric by virtue of two aspects of their structure. First, the fusion protein is chimeric in that it includes an immunoglobulin chain (typically but not exclusively a heavy chain) of appropriate antigen-binding specificity fused to a given heterodimeric cytokine. Second, an immunoconjugate of the invention may be chimeric in the sense that it includes a variable region and a constant region which may be the constant region normally associated with the variable region, or a different one and thus a V/C chimera; e.g., variable and constant regions from different species. Also embraced within the term "fusion protein" are constructs having a binding domain comprising framework regions and variable regions (i.e., complementarity determining regions) from different species, such as are disclosed by Winter, et al., GB2, 188, 638.

The heterodimeric cytokine-antibody fusion protein of the present invention preferably displays antigen-binding specificity. In a preferred embodiment, the heterodimeric cytokine-antibody fusion protein comprises a heavy chain. The heavy chain can include a CH1, CH2, and/or CH3 domains. In an alternative preferred embodiment, the heterodimeric cytokine-antibody fusion protein comprises a light chain. The invention thus provides fusion proteins in which the antigen binding specificity and activity of an antibody are combined with the potent biological activity of a heterodimeric cytokine. A fusion protein of the present invention can be used to deliver selectively a heterodimeric cytokine to a target cell in vivo so that the heterodimeric cytokine can exert a localized biological effect.

Preferably, the fusion protein of the present invention displays cytokine biological activity. The preferred heterodimeric cytokine of the fusion protein is IL-12. Fusions with antibodies capable of binding antigens are useful for co-localizing the immune stimulatory activity of IL-12 either to target cells or target protein antigens.

Further, the fusion protein of the present invention preferably has a longer circulating half-life than an unlinked heterodimeric cytokine. Fusions with the Fc portion of antibodies and IL-12 are useful for altering the pharmacology and biodistribution of the molecule by increasing its circulating half-life and its affinity for Fc-receptor bearing cells, e.g. antigen presenting cells. Changes in biodistribution may also alter its systemic toxicity by changing the mechanism by which it is cleared from the circulation.

In another aspect of the invention, the fusion proteins comprise a heterodimeric cytokine linked to an antigen. The preferred heterodimeric cytokine-antigen fusion protein of the present invention displays cytokine biological activity and antigenic activity. Further, the fusion protein of the present invention preferably has a longer circulating half-life than an unlinked heterodimeric cytokine. The preferred heterodimeric cytokine of the fusion protein is IL-12.

In a preferred embodiment, the fusion protein comprises two chimeric chains linked by a disulfide bond. Each chimeric chain comprises a different subunit of the heterodimeric cytokine, either of which is linked through a peptide bond to an antigen.

In an alternative preferred embodiment, the fusion protein comprises a first chimeric chain comprising one of the subunits of the heterodimeric cytokine linked by a peptide bond to an antigen. This subunit is linked by a disulfide bond to the other subunit of the heterodimeric cytokine. In another alternative preferred embodiment, this first chimeric chain is linked by a disulfide bond to a second chimeric chain comprising one of the subunits of the heterodimeric cytokine linked by a peptide bond to an antigen and by a disulfide bond to the other subunit of the heterodimeric cytokine.

In another alternative preferred embodiment, the fusion protein is a trimeric fusion protein comprising a first and a second chimeric chain linked by a disulfide bond. Each chimeric chain comprises a subunit of the heterodimeric cytokine linked by a peptide bond to an antigen. The subunit of one of the chimeric chain is further linked by a disulfide bond to a different subunit of the heterodimeric cytokine.

The invention also features DNA constructs encoding the above-described fusion proteins, and cell lines, e.g., myelomas, transfected with these constructs.

The invention also includes a method for selectively targeting a heterodimeric cytokine. In a preferred embodiment, the method comprise linking at least one subunit of a heterodimeric cytokine by a peptide bond to a portion of an Ig heavy chain. In an alternative preferred embodiment, the method comprise linking each of the two subunits of a heterodimeric cytokine by a peptide bond to a portion of an Ig heavy chain, thereby forming two chimeric chain. The two chimeric chains are linked by a disulfide bond, thereby forming a heterodimeric fusion protein. In yet another preferred embodiment, the method comprises (1) linking one of the two subunits of a first heterodimeric cytokine by a peptide bond to an Ig heavy chain, thereby forming a first chimeric chain; (2) linking one of the two subunits of a second heterodimeric cytokine by a peptide bond to an Ig heavy chain, thereby forming a second chimeric chain; and (3) linking the first and second chimeric chains by a disulfide bond, thereby forming a fusion protein. The resulting fusion proteins can display binding specificity for a predetermined antigen and cytokine biological activity.

The invention also includes a method of selectively delivering a heterodimeric cytokine to a target cell. The method includes providing a heterodimeric cytokine fusion protein including a chimeric Ig chain including an Ig heavy chain having a variable region specific for an epitope on the target cell and a constant region joined at its carboxy terminus by a peptide bond to a cytokine, and an Ig light chain combined with the chimeric Ig heavy chain, forming a functional antigen-binding site, and administering the fusion protein in an amount sufficient to reach the target cell to a subject harboring the target cell.

Further, the invention features a method of increasing the circulating half-life of a heterodimeric cytokine. In a preferred embodiment, the method comprise linking at least one subunit of a heterodimeric cytokine by a peptide bond to a polypeptide. In an alternative preferred embodiment, the method comprises linking each of the two subunits of a heterodimeric cytokine by a peptide bond to a polypeptide, thereby forming two chimeric chain. The two chimeric chains are linked by a disulfide bond, thereby forming a heterodimeric fusion protein. In yet another preferred embodiment, the method comprises (1) linking one of the two subunits of a first heterodimeric cytokine by a peptide bond to a polypeptide, thereby forming a first chimeric chain; (2) linking one of the two subunits of a second heterodimeric cytokine by a peptide bond to a polypeptide, thereby forming a second chimeric chain; and (3) linking the first and second chimeric by a disulfide bond, thereby forming a fusion protein. The polypeptide can be serum albumin, an antigen, and a portion of an Ig heavy chain. The resulting fusion proteins display cytokine biological activity.

The IL-12 fusion proteins of the present invention are useful for specific targeting or immune stimulation when it is important to generate a cell-mediated immune response, such as in cancer immunotherapy or antiviral responses. They are also useful for specifically downregulating Th2 responses which often lead to the overproduction of IL-4. This cytokine has been shown to be essential for the development of allergy through the induction of a Th2 response and the resulting overproduction of IgE antibody.

BRIEF DESCRIPTION OF THE DRAWINGS

The foregoing and other objects of the present invention, and the various features thereof, may be more fully understood from the following description, when read together with the accompanying drawings, in which.

DETAILED DESCRIPTION OF THE INVENTION

The present invention describes fusion proteins between heterodimeric cytokines and other proteins. Heterodimeric cytokines can be fused to, for example, proteins with targeting or antigenic properties. Fusion proteins between heterodimeric cytokines and proteins with targeting or antigenic properties may have a longer circulating half life than unlinked heterodimeric cytokines. Targeting or antigenic properties are not required for the increased circulating half life as this property can also be achieved by fusing a heterodimeric cytokine with a protein that lacks targeting or antigenic properties such as, for example, serum albumin.

Figure 1A:
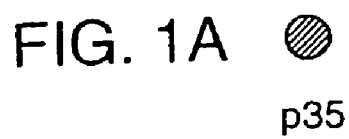
FIG. 1 is a diagrammatic representation of the predicted protein structure of heterodimeric fusion proteins.
Figure 1B:
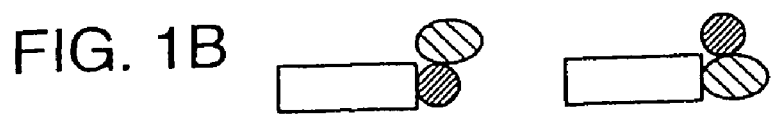
Figure 1C:
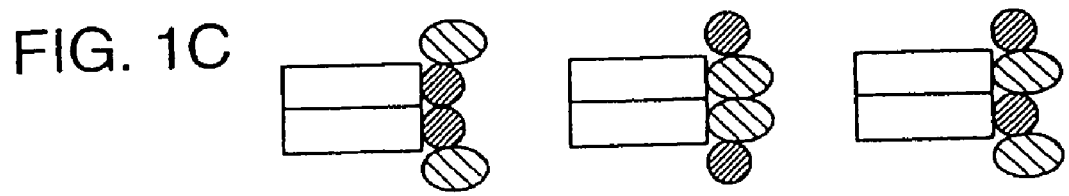
Figure 1D:
Figure 1E:
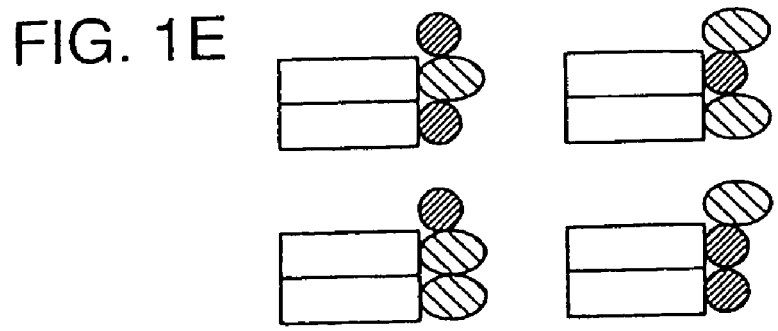

The fusion proteins of this invention can be produced by genetic engineering techniques. As depicted in FIG. 1, various fusion protein constructs can be produced by the methods of the present invention. In one embodiment, one of the subunit of the heterodimeric cytokine fused to a polypeptide is co-expressed with a free subunit of the other type. Once expressed, the chimeric chain is linked by a disulfide bond to the free subunit (FIG. 1B). In another embodiment, the polypeptide fused with one of the subunit can be linked to another such polypeptide. Since each polypeptide is linked to a heterodimeric cytokine, the resulting construct has two molecules of the heterodimeric cytokine (FIG. 1C). In yet another embodiment, each of the subunit of the heterodimeric cytokine is fused to a polypeptide and the two chimeric chains are linked by a disulfide bond. The resulting construct has only one molecule of the heterodimeric cytokine (FIG. 1D). In yet another embodiment, two subunits of the heterodimeric cytokine fused to a polypeptide are co-expressed with a free subunit. The resulting construct has three subunits of the heterodimeric cytokine (FIG. 1E).

At present, the only known heterodimeric cytokine is IL-12. However, as novel heterodimeric cytokines are identified and sequenced, a skilled artisan will be able to use methods of the present invention to produce fusion proteins with these novel heterodimeric cytokines.

Methods for synthesizing useful embodiments of the invention are described, as well as assays useful for testing their pharmacological activities, both in vitro and in preclinical in vivo animal models. The preferred gene construct encoding a chimeric chain (i.e., a subunit of the heterodimeric cytokine fused to a polypeptide) includes, in 5' to 3' orientation, a DNA segment which encodes a polypeptide and DNA coding for one subunit of the heterodimeric cytokine. An alternative preferred gene construct includes, in 5' to 3' orientation, a DNA segment which encodes one subunit of the heterodimeric cytokine and DNA coding for a polypeptide. The fused gene is assembled in or inserted into an expression vector for transfection of the appropriate recipient cells where it is expressed.

The invention is illustrated further by the following non-limiting examples:

EXAMPLE 1

Cloning cDNAs Encoding Human and Mouse IL-12 Subunits

Human peripheral blood monocytes (PBMC) were obtained from a healthy volunteer and were purified by centrifugation on a Ficoll-Hypaque (Pharmacia) gradient (1700 rpm for 20 nm). The "buffy" coat containing the PBMC was diluted with serum-free culture medium (SF-RPMI) to a volume of 50 ml and collected by centrifugation at 1500 rpm for 5 min. Cells were resuspended in AIM-V cell culture medium (GIBCO) at a density of 5×10⁶ cells/ml and were cultured for 2 days at 37° C. in a humidified $CO_2$ incubator. The attached cells were selected by gently agitating the culture flask to remove non-adherent cells. Fresh medium containing phorbol ester (100 nM) and the calcium ionophore, ionomycin (0.1 μg/ml) was added. After three days, the cells were collected by gentle scraping and centrifugation. Poly A+ mRNA wvas prepared using oligo dT-coated beads (Dynal, Inc.).

Subunit cDNAs were cloned using polymerase chain reactions (PCR). First strand cDNA was synthesized in a 50 μl reaction containing oligo dT primer (50 μg/ml), reaction buffer, RNAsin (10 U/ml) and reverse transcriptase. Incubation was at 43° C. for 2 hrs, followed by extraction with phenol, phenol:chloroform (50:50) and precipitation with ethanol. The cDNA product was used as template for PCR reactions containing Taq polymerase and reaction buffer (10× buffer; Perkin Elmer), sense and antisense primers (0.2 to 0.5 μM each), and 10% of the cDNA reaction. Primer sequences were 5'-CCAGAAAGCAAGAGACCAGAG-3' (SEQ ID NO: 1) for the sense primer, and 5'-GGAGGGACCTC- GAGTTTTAGGAAGCATTCAG-3' (SEQ ID NO: 2) for the antisense primer of the p35 subunit cDNA. The sense primer is derived from a sequence in the 5' untranslated region of the p35 message just upstream of a XmaI site, while the antisense primer encodes a translational stop codon followed shortly thereafter by a convenient XhoI site for directional subcloning in an expression vector. The primers for the p40 subunit cDNA were 5'-CTCCGTCCTGTCTAGAGCAAGATGT-GTC-3' (SEQ ID NO: 3) for the sense and 5'-GCTTCTC-GAGAACCTAACTGCAGGGCACAG-3' (SEQ ID NO: 4) for the antisense primer. The sense primer encodes a unique XbaI site upstream of the translation start site while the antisense primer encodes a stop codon and unique XhoI site as above. Both subunit sequences, cloned with these PCR primers, will be expressed as single proteins and thus require native (or other) secretory leader sequences for proper heterodimer assembly and secretion. PCR reactions consisted of 40 cycles including: 1 min at 92° C., 2 min at 52° C., and 3 min at 72° C., following an initial denaturation step at 94° F. for 2 min. Products were gel purified and cloned in the SK cloning vector (Strategene) for sequence verification. DNA sequencing using a commercial kit (U.S. Biochemical) was carried out on each of the subunit cDNA. The same procedure can be used to clone the mouse p35 subunit cDNA from spleen cells activated with Concanavalin A (5 µg/ml in culture medium for 3 days). Recommended primers are 5'-CCTCTACTAACAT-GTGTCAATCACGCTACCTC-3' (SEQ ID NO: 5) for the sense and 5'-CCCTCGAGTCAGGCGGAGCTCAGAT-AGCC-3' (SEQ ID NO: 6) for the antisense primers encoding the same restriction sites as described above for the human p35 subunit.

EXAMPLE 2

Expression of Fusion Protein Combinations in Transfected Mammalian Cells

In order to make the fused versions of each subunit, the DNAs encoding the mature protein sequence of each were adapted as follows. The p40 subunit DNA was digested with NdeI which cuts very close to the junction of the mature protein and leader sequence, and XhoI. An adapter oligonucleotide was synthesized with the sequence 5'-CCGGGCAAGTCCA-3' (SEQ ID NO: 7) hybridized to a second, partly complementary oligonucleotide with the sequence 5'-TATGGACTTGC-3' (SEQ ID NO: 8). The double stranded DNA contains overhanging sequence compatible with ligation to an XmaI site at the 5' end and an NdeI site at the 3' end. This fragment was ligated to the NdeI-XhoI fragment of the p40 cDNA and cloned as an XmaI to XhoI fragment in vector pdC-Fc-X, cut with XmaI and XhoI. This vector already contains a human IgG1 Fc encoding DNA fragment in its genomic configuration (containing introns and exons) and fused downstream of a leader sequence derived from a mouse light chain. See, Gillies, et al., *J. Immunol. Methods* 125: 191-202 (1989). The addition of a DNA fragment to its unique XmaI site allows for the production of fusion proteins joined directly to the carboxyl terminus of the Fc, provided that the reading frame between the two sequences is maintained (Lo, et al., U.S. Pat. No. 5,541,087). Other proteins (e.g., antigen, serum albumin) can be fused to the amino termini of these subunits in the same manner. The advantages of this method include the large quantities of product produced and the ease of purification of the product by binding to and elution from protein A Sepharose.

The same general strategy was used to fuse the p35 subunit DNA to human Fc. In this case, a XmaI-BalI linker was synthesized using the oligonucleotides 5'-CCGGGAA-GAAACCTCCCCGTGG-3' (SEQ ID NO: 9) and 5'-CCACGGGGAGGTTTCTTC-3' (SEQ ID NO: 10), which were ligated to a p35 subunit DNA, cut with BalI and XhoI, and subcloned as an XmaI-XhoI fragment in the pdC-Fc-X vector, as described above. The human p35 subunit has been shown to be active for human cells but not mouse cells, in terms of IL-12 activity, whereas the human p40 subunit does not show species specificity. Therefore, the human p40 subunit can be used to make either all human IL-12 fusion proteins or hybrid human/mouse fusion proteins.

The resulting constructs encode Fc-p35 or Fc-p40 fusion proteins which are expected to spontaneously dimerize into proteins of 120 kD (50 Kd from the Fc) and 130 kD respectively and to migrate after reduction on denaturing SDS gels as proteins of 60 kD and 65 kD. The individual subunit cDNAs were subcloned in the pdC expression vector (without the Fc) for their expression as independent proteins. This vector provides promoter sequences for expression of mRNA, transcribed from the cDNA insert, following the transfection of mammalian cells. It also provides for a 3' untranslated region and poly A addition site, downstream of the 3' XhoI insertion site. There are also sequences necessary for the propagation of the plasmid in *E. coli* and selection with ampicillin, as well as a selectable marker gene, such as dihydrofolate reductase (dhfr), for conferring resistance to methotrexate. These same components are also used in the pdC-Fc-X vector for expression of the fusion proteins.

For expression of biologically-active IL-12 fusion protein heterodimers, different combinations of the individual vectors encoding fusion and non-fusion forms of the subunits were transiently expressed by co-transfection of human 293 epidermal carcinoma cells. DNA was purified using preparative kits (Wizard, Promega Inc.), ethanol precipitated for sterilization and resuspension in sterile water. Calcium phosphate precipitates were prepared by standard methods using 10 µg of DNA per ml (5 µg of each when two plasmids were co-transfected) and 0.5 ml/plate were added to cultures of 293 growing in 60 mm plates at approximately 70% confluency. MOLECULAR CLONING A LABORATORY MANUAL, 2nd Ed. (Sambrook, Fritsch and Maniatis, eds., Cold Spring Harbor Laboratory Press, 1989). After 16 hr, the medium containing the precipitate was removed and replaced with fresh medium. After 3 days, the supernatant was removed and analyzed for production of transfected gene expression by ELISA, biological determination of IL-12 activity, or immunoprecipitation and analysis on SDS gels of radioactively labeled proteins. For labeling, medium without methionine was used to replace the growth medium on the second day of culture and $^{35}$S-methionine (100 µCi/ml) is added. After an additional 16 hr incubation, the media was harvested, clarified by centrifugation (5 min at 13,000 rpm in a table top microcentrifuge) and incubated with protein A Sepharose beads (10 µl of bead volume per ml of culture supernatant). After 1 hr at room temperature, the beads were washed by repeated centrifugation and resuspension in PBS buffer containing 1% NP-40. The final pellet was resuspended in SDS-containing gel buffer and boiled for 2 min. After removing the beads by centrifugation, the supernatant was divided into two aliquots. Reducing agent (5% 2-mercaptoethanol) was added to one sample and both are boiled for 5 min prior to loading on an SDS polyacrylamide gel. After electrophoresis the gel was exposed to X-ray film (autoradiography).

Figure 2:
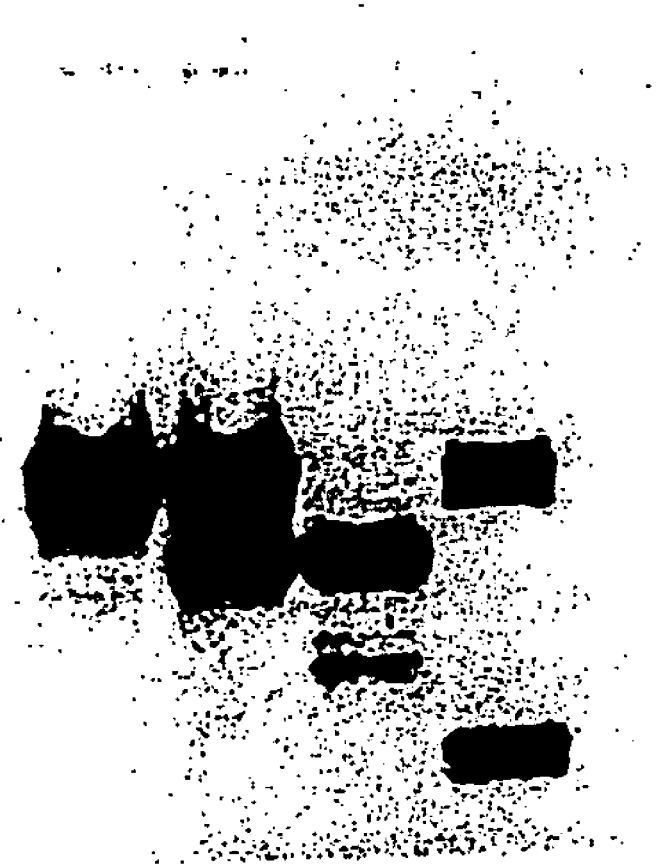
FIG. 2 is a diagrammatic representation of an SDS-PAGE showing an analysis, under reducing conditions, of proteins secreted by cells transfected with vectors expressing the Fc-p35 fusion protein (lane 1), the Fc-p40 fusion protein (lane 2), the Fc-p35 fusion protein and the Fc-p40 fusion protein (lane 3), the Fc-p35 fusion protein and the p40 subunit (lane 4), and the p35 subunit and the Fc-p40 fusion protein (lane 5)
Figure 3:
FIG. 3 is a diagrammatic representation of the predicted protein structure of expressed fusion proteins.
Figure 3:
Figure 3:
Figure 3:
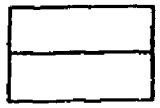
Figure 3:
Figure 3:
Figure 3:
Figure 3:
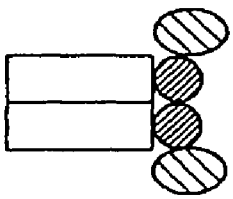
Figure 3:
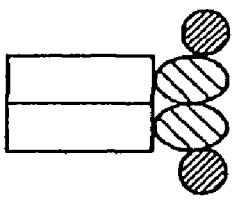

An example of an analysis of the co-expression of various fusion proteins and individually expressed proteins, under reducing conditions, is show in FIG. 2. The results show that the p35 subunit cannot be secreted from the cell, even when expressed as a fusion protein with the Fc fragment (lane 1). The p40 subunit, on the other hand, was readily secreted when fused to Fc (lane 2). The p35 subunit as secreted when it could pair with the p40 subunit, either as an Fc-p35 fusion pairing with an Fc-p40 fusion protein (lane 3), the Fc-p35 pairing with free p40 (lane 4), or free p35 pairing with the Fc-p40 fusion protein (lane 5). In all cases of expression of a free subunit, together with a fusion protein, the free subunit assembles with the other subunit and forms a covalent, disulfide bond. A diagram of these various combinations is shown in FIG. 1. Note that the construct with each subunit fused to Fc and co-expressed in the same cell has one molecule of IL-12 per Fc (FIG. 1D), whereas the constructs with a single subunit fusion to Fc paired with a free subunit (of the other type) has two molecules of IL-12 per Fc (FIG. 1C). Expression in stably transfected cells is expected to be different from transient expression since the expression and secretion is independent of p35. Thus, overexpression of p40 is possible and more advantageous to the cell since it can easily be exported. This could lead to an overabundance of Fc-p40 subunits relative to Fc-p35 and result in a mixture of heterodimer and p40 homodimer secretion from the cell. This would be inefficient and lead to purification problems. Expression of p35 is likely to have a growth disadvantage, since excess protein is likely degraded in the endoplasmic reticulum, unless it is effectively paired with the p40 subunit. Thus, it is possible to take advantage of this situation to ensure the balanced secretion of only heterodimer fusion product, by expressing the p35 subunit as a fusion protein together with free p40 subunit. Only p35 fusion protein paired with an equimolar amount of p40 subunit can be secreted. Purification of this product on protein A results in a homogeneous preparation of heterodimer. A diagrammatic representation of the predicted protein structure of expressed fusion proteins is provided in FIG. 3.

EXAMPLE 3

Activity of Fusion Proteins on in an IFN-γ Induction Assay

Biological activity was measured in an IFN-γ induction assay using mitogen-activated human PBMC, purified as described in Example 1. After gradient centrifugation, cells were resuspended in cell culture medium containing 10% fetal bovine serum (RPMI-10) and phytohemaglutinin (PHA; 10 μg/ml) at a density of $5\times10^6$ cells/ml and were cultured for 3 days at 37° C. in a humidified $CO_2$ incubator. The PHA-activated cells were collected by centrifugation, washed three times with an equal volume of SF-RPMI and resuspended in fresh RPMI-10 ($1\times10^6$ cells/ml). Aliquots (100 μl) were dispensed into the wells of multiple 96-well plates to give a final cell number of $10^5$ per well. Test samples from culture medium were serially diluted in fresh culture medium and added to wells of the 96-well plate Stimulation medium (50 μl/well) containing 10% serum and IL-2 (25 U/ml) was added. Control wells received only IL-2 (negative control) or both IL-2 and commercial IL-12 (R & D Systems) but no sample (positive control). The plates were incubated for 48 hr at 37° C. in a $CO_2$ incubator at which time aliquots (20 μl) were removed for analysis of IFN-γ concentration by ELISA.

The same assay was used to determine the activity of mouse forms of IL-12 fusion proteins, except that spleen cells from Balb/c mice activated for 3 days with Concanavalin A, were used instead of PHA-activated human PBMC. A mouse-specific ELISA was used to quantitate the amount of IFN-γ induced by the human p40/mouse p35 hybrid molecules from mouse cells.

For the human system, a quantitative ELISA was developed by coating 96-well plates (Nunc-Immuno plate F96 Cert. Maxisorb) with a mouse monoclonal antibody against human IFN-γ (1 μg/ml) in phosphate buffered saline (PBS; Pestka Biological Laboratories) overnight at 4° C., washing unbound antibody three times with PBS, and blocking with a solution of 1% bovine serum albumin (BSA) and 1% goat serum in PBS (150 μl/well for 2 hr at 37° C.). After washing the blocked plates four times with PBS, test samples and dilutions of the IFN-γ standard were added in a final volume of 100 μl/well. Following an overnight incubation at 4° C., the plates were washed four times with PBS, and a polyclonal rabbit antiserum against human IFN-γ (1/10000 dilution; Petska Biological Laboratories) was added. After an additional incubation for 1 hr at 37° C. and four washes with PBS, a polyclonal donkey anti-rabbit detecting antibody, conjugated to horse radish peroxidase (1/700 dilution; Petska Biological Laboratories) was added for 1 hr at 37° C. The plates are then washed four times with PBS and 100 μl of K-blue substrate (ELISA Technologies, Neogen Corp.) was added until the color in the wells containing the standard curve was sufficiently developed, at which time 100 μl of Red-stop solution (ELISA Technologies) was added. The plate was read at 650 nm using an ELISA plate reader (Dynatech MR7000) and the amount of IFN-γ was calculated by comparing the optical density of the test sample with a standard curve derived from the dilutions of the control IFN-γ. The amount of IFN-γ that was induced in the presence of both IL-2 and IL-12 generally ranges from 1200-2000 pg/ml while the amount produced in the absence of IL-12 was generally less than 50 pg/ml.

Figure 4:
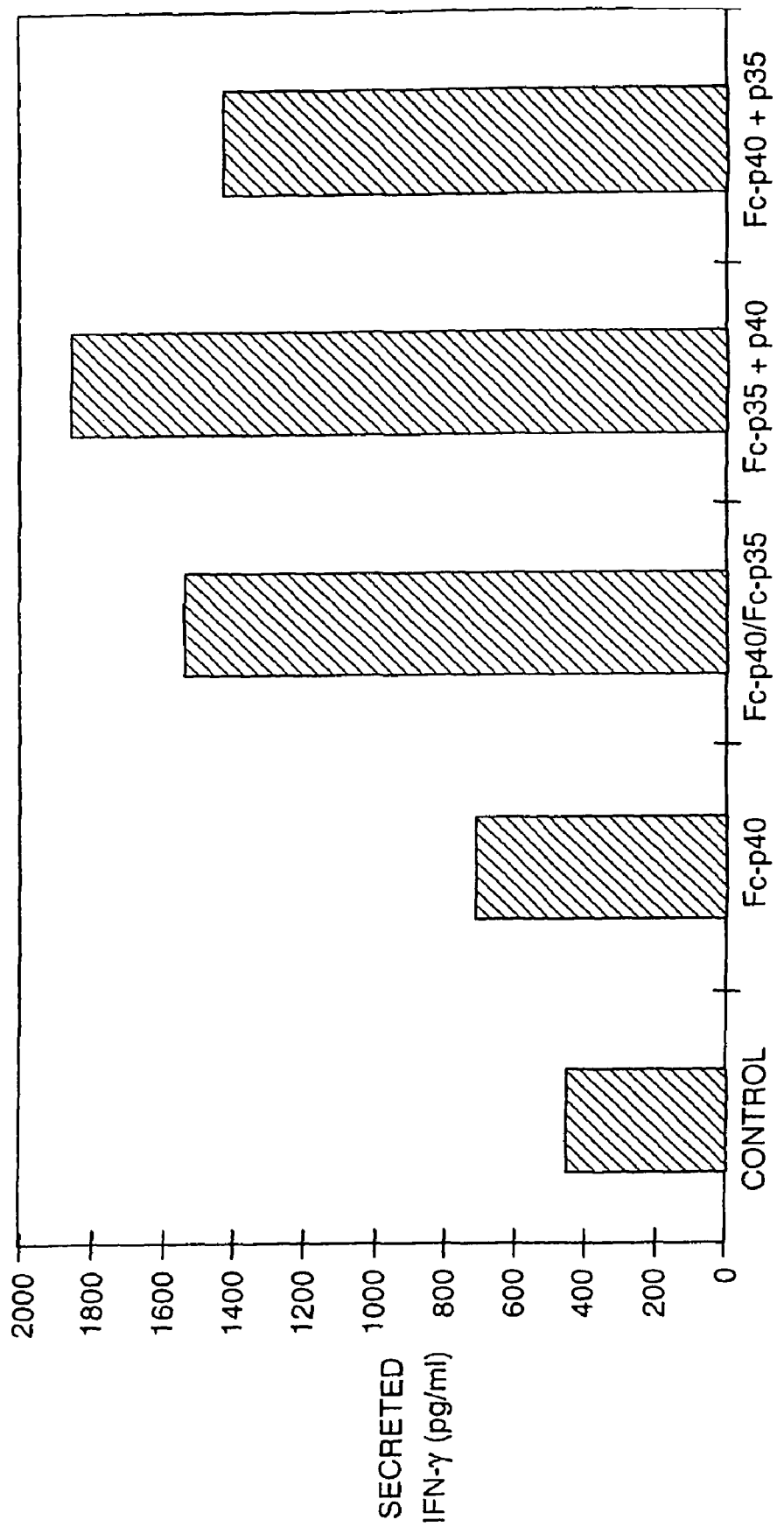
FIG. 4 is a bar graph depicting the ability of various fusion proteins to stimulate IFN-γ production.

The biological activity of the culture supernatants described in Example 2 were compared for their ability to stimulate IFN-γ production. As depicted in FIG. 4, the highest activity was obtained with the FC-p35 fusion protein co-expressed with free p40 subunit, although the other combinations with both subunits were also active. More accurate measurements with purified proteins are described below.

EXAMPLE 4

Expression of Antibody-IL-12 Fusion Proteins

The experiments described in Example 2 demonstrate that a convenient way to express fusion proteins with the IL-12 heterodimeric cytokine is to co-express a fused p35 subunit protein together With the free p40 subunit in the same cell. This can be done by two approaches: the first is achieved by co-transfecting the fusion protein vector and the p40 expression vector simultaneously (i.e., simultaneous transfection); the second is to first transfect a cell with p40 alone and select for high level, stable secretors of this protein, and then use this cell as a recipient for transfection by the fusion protein expressing construct (i.e., sequential transfection). The latter method is particularly useful when the fusion protein is an antibody molecule with both a heavy and light chain that need to be assembled properly for correct assembly and secretion. Theoretically, the fusion of p35 subunit could be to the heavy or light chain, but the preferred embodiment would be to the carboxyl terminus of the heavy chain, where it can be more free to interact with the IL-12 receptor on cells. It is also possible to fuse the p35 subunit via its carboxyl terminus to the amino terminus of the heavy or light chain. In this case, a leader sequence would be required for p35 expression, since it would be at the amino terminus of the fusion protein, thus requiring its direction to the endoplasmic reticulum for assembly and secretion from the cell.

The nucleic acid construct can also include the endogenous promoter and enhancer for the variable region-encoding gene to regulate expression of the chimeric immunoglobulin chain. For example, the variable region encoding genes can be obtained as DNA fragments comprising the leader peptide, the VJ gene [functionally rearranged variable (V) regions with joining (J) segment] for the light chain or VDJ gene for heavy chain, and the endogenous promoter and enhancer for these genes. Alternatively, the gene coding for the variable region can be obtained apart from endogenous regulatory elements and used in an expression vector which provides these elements.

Variable region genes can be obtained by standard DNA cloning procedures from cells that produce the desired antibody. Screening of the genomic library for a specific functionally rearranged variable region can be accomplished with the use of appropriate DNA probes such as DNA segments containing the J region DNA sequence and sequences downstream. Identification and confirmation of correct clones are then achieved by DNA sequencing of the cloned genes and comparison of the sequence to the corresponding sequence of the full length, properly spliced mRNA.

4.1 Simultaneous Transfection

Simultaneous transfection can be achieved by constructing a vector with two transcription units and a selectable marker gene. Such vectors are described for the expression of recombinant antibodies in mammalian cells. Gillies, et al., *J. Immunol. Methods* 125: 191-202 (1989). An alternative method is to use two independent plasmid vectors (one with a transcription unit for the fusion protein and one with a transcription unit for the p40 subunit) with their own selectable marker genes, and to select for successfully transfected, expressing cells by culturing in the presence of the drugs to which the cells have become resistant (e.g., methotrexate in cells transfected with the dhfr gene). Still another approach would be to use an expression vector for the fusion protein to the p35 subunit containing a selectable marker gene and co-transfecting a second vector with no selectable marker gene and a transcription unit for the p40 subunit. Any drug resistant clone obtained by the latter method could not secrete the fusion protein in the absence of the p40 subunit and thus, would not be detected by an ELISA assay of the culture supernatant. Only cells transfected with both vectors would secrete the intact fusion protein-p40 heterodimer.

A plasmid vector (pdHL7-14.18-p35) was constructed, as described in Gillies, et al., *J Immunol. Methods* 125: 191-202 (1989), that contains a dhfr-selectable marker gene, a transcription unit encoding a humanized 14.18 anti-GD2 antibody light chain, and a transcription unit encoding a humanized heavy chain fused to the p35 subunit of human IL-12. The fusion was achieved by ligation of the XmaI to XhoI fragment of the adapted p35 subunit cDNA, as described in Example 2, to a unique XmaI site at the end of the CH3 exon of the human IgG1 H chain gene. Both the H and L chain transcription units include a cytomegalovirus (CMV) promoter (in place of the metallothionein promoter in the original reference) at the 5' end and a poly adenylation site at the 3' end. A similar vector (pC-p40) was constructed for expression of the free p40 subunit but did not include a selectable marker gene (dhfr or other) but still used the CMV promoter for transcription. The coding region in this case included the natural leader sequence of the p40 subunit for proper trafficking to the endoplasmic reticulum and assembly with the fusion protein. Another version of this vector (pNC-p40), which includes the neomycin resistance gene, was constructed for use in sequential transfection.

For simultaneous transfection, plasmid DNAs (approximately 10 μg of each plasmid; pdHL7-14.18-p35 and pC-p40) were linearized by digestion with SalI restriction enzyme, purified using PCR Cleanup kit (Wizard, Promega), and electroporated into $5 \times 10^6$ myeloma cells (in 0.5 ml ice cold PBS) using a setting of 0.25 volts and 500 μF. After a recovery for 10 min on ice, cells were transferred to fresh medium and plated in 96-well dishes at approximately $10^5$ cells/ml. After 48 hr, cells were fed with medium containing methotrexate (0.1 μM). Fresh medium was added by exchange of half the fluid volume every 4 days until clones appeared. Expression of the desired antibody-IL-12 fusion protein was assayed using an ELISA based on antibody Fc detection. The capture antibody reacted with human H and L chains, and the detection utilized an antibody specific for human Fc. Positive clones were expanded in selection medium and the product was purified by binding to and elution from protein A Sepharose as described above Eluted proteins were analyzed by PAGE and detected by staining with Coomassie Blue.

4.2 Sequential Transfection

For sequential transfection, plasmid pNC-p40 was electroporated into cells, as described above, and cells were plated and selected in G418-containing medium. Culture supernatants from drug-resistant clones were tested by ELISA for production of p40 subunit. The capture antibody was a mouse anti-human IL-12 p40 and the detecting antibody was directed to human IL-12 p40/p70. Commercial ELISA kits are available from several manufacturers for this purpose (Phaminogen, San Diego; R & D Systems, N4N). The highest producing cell clones were tested for the stable expression of p40. One such clone was transfected with pdHL7-14.18-p35 plasmid DNA, as described above, and clones were selected in methotrexate-containing medium. Expression of the desired antibody-IL-12 fusion protein was assayed using an ELISA based on antibody Fc detection. The capture antibody reacted with human H and L chains, and the detection utilized an antibody specific for human Fc. Positive clones were expanded in selection medium and the product was purified by binding to and elution from protein A Sepharose as described above. Eluted proteins were analyzed by PAGE and detected by staining with Coomassie Blue.

4.3 Activities of Antibody-IL-12 Fusion Proteins

Figures 5A, 5B:
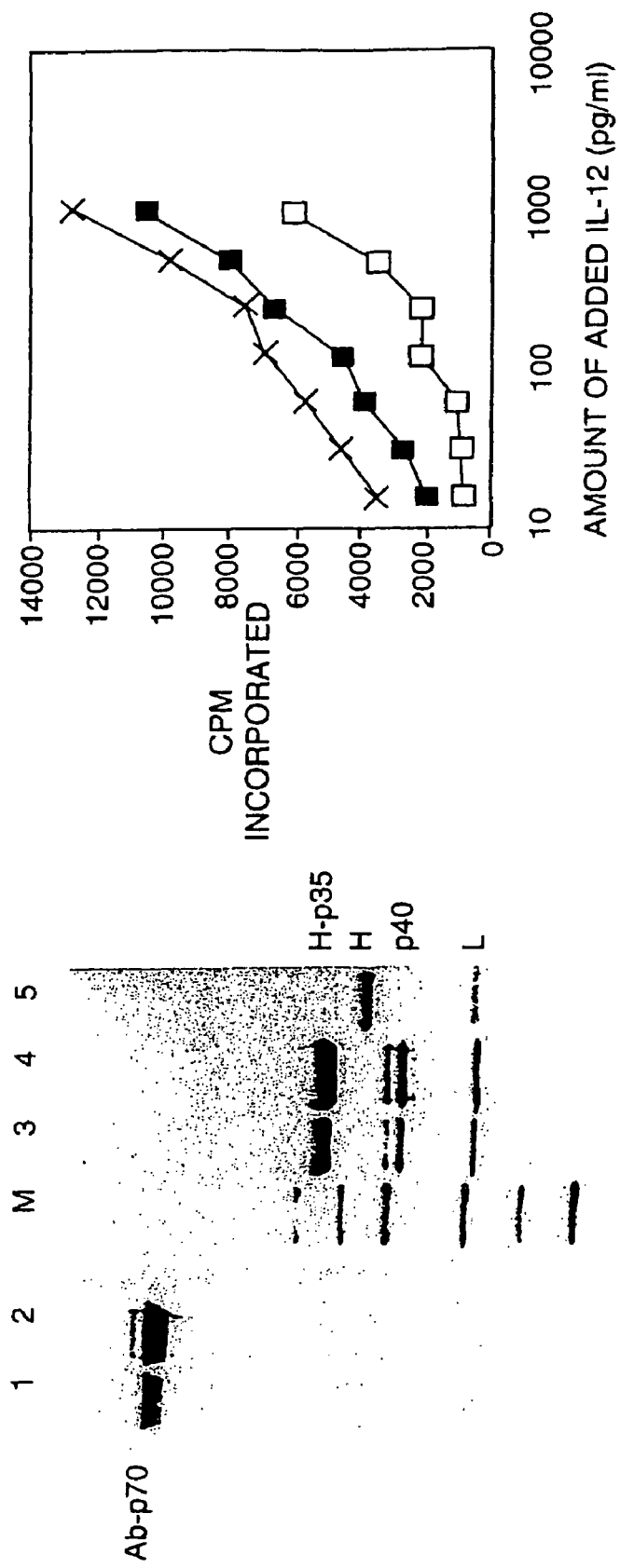
FIG. 5A is a diagrammatic representation of an SDS-PAGE showing an analysis of whole antibody-IL-12 fusion proteins produced by two independent transfectants, under non-reducing (lanes 1 and 2) and reducing conditions (lanes 3 and 4)
FIG. 5B-D are line graphs depicting the effects of human IL-12 (X), Hu-KS-IL-12 fusion protein with both human IL-12 chains (closed squares), and Hu-KS-1/4-mouse p35 human p40 fusion protein (open squares) on proliferation of mitogen-activated human PBMC (Panel B); induction of IFN-γ secretion from PHA-activated PBMC (Panel C) and from mouse effector cells, pre-stimulated with Concanavalin A (Panel D)

As summarized in Table 1, fusion protein-expressing cell clones were obtained by either simultaneous transfection and sequential transfection but more highly productive clones were obtained using sequential transfection. The product secreted by two individual transfectants were analyzed for chain composition. The SDS-PAGE analysis is shown in FIG. 5A. Clearly, both clones secrete the same relative amount of each of the three chains: light chain, H chain-p35, and covalently bound p40, indicating complete and proper assembly of this 6-chain molecule. The same process was repeated with a second antibody, KS-1/4, reactive with the EpCAM antigen expressed on virtually all epidermal carcinoma cells (colon, lung, breast, prostate, pancreatic, ovarian, and bladder carcinoma). Exactly the same results were obtained, including normal binding activities of the antibodies to their respective antigens.

Figures 5C, 5D:
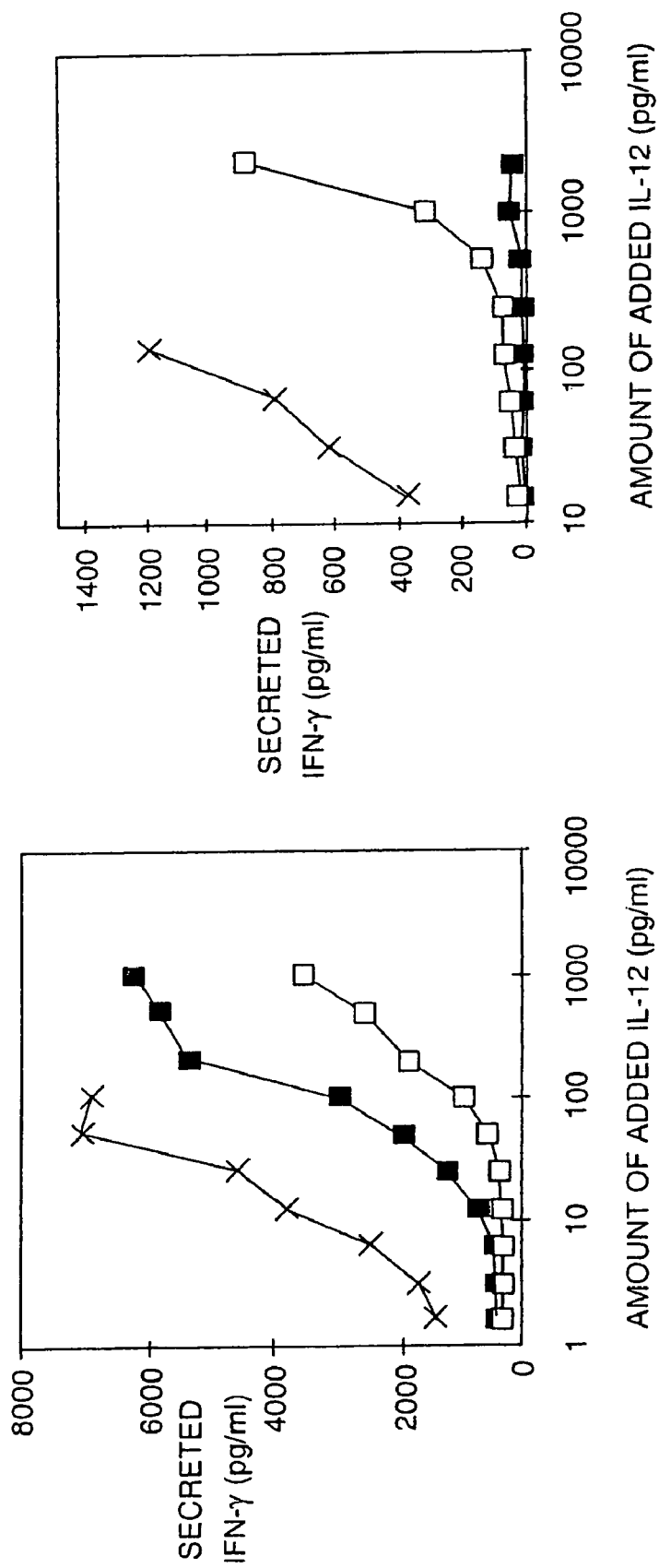

The biological activities of the whole antibody-IL-12 fusion proteins are shown in FIG. 5. When assayed for ability to stimulate proliferation of mitogen-activated human PBMC, the Hu-KS-IL-12 fusion protein with both human IL-12 chains was nearly as active on a molar basis as the human IL-12 standard (FIG. 5B). The same construct containing the mouse p35 subunit fused to Hu-KS-1/4 was significantly less active in the stimulation of human PBMC. When assayed for ability to induce IFN-γ secretion from PHA-activated PBMC, the Hu-KS-IL-12 protein with human IL-12 chains was about 6-fold less active than the IL-12 standard, while the hybrid form was an additional 4-fold less active (FIG. 5C). When mouse effector cells (pre-stimulated with Concanavalin A) were used, the hybrid form was about 50-fold less active than the mouse IL-12 standard. The all-human form was inactive (FIG. 5D), as expected from the literature. See, Schoenhaut, et al., *J Immunol.* 148: 3433-3340 (1992).

TABLE 1

Comparison of Co-transfection and Sequential
Transfection of IL-12 Fusion Protein Expression

| Method | Frequency of Positive Clones | Expression Level (ng/ml) |
|---|---|---|
| Co-transfection | 4/22 | 20, 22, 244, 386 |
| Sequential | 26/37 | 18, 19, 19, 45, 48, 60, 67, 93, 97, 128, 177, 244, 256, 345, 348, 366, 371, 386, 504, 554, 731, 757, 821, 2000 |

EXAMPLE 5

Expression of Single Chain IL-12 Fusion Proteins

The methods just described for the production of dimeric antibody and Fc-based fusion proteins can also be used in its simpler form to express single chain fusion proteins with IL-12 (those not forming dimers). In this case, a single polypeptide encoding sequence is joined to the sequence for the p35 subunit and co-expressed in the same cell as the free p40 subunit. Either of the two methods, simultaneous or sequential transfection, can be used to produce single-chain heterodimeric fusion proteins. The purpose of such fusion proteins can be either to target IL-12 to an antigen bearing cell, through the fusion of a single-chain Fv (sc-Fv) antibody (Huston and Oppermann, WO 88/09344) or to combine the very specific immunostimulatory effect of IL-12 together with a protein antigen as an adjuvant. The linking of stimulatory protein and antigen ensures their co-localization following injection into an animal. The antigen can be any polypeptide. These can induce antibodies in animals capable of reacting with tumor, viral or other antigens that have therapeutic value. For example, sc-Fv can be used as it is often advantageous to induce immune responses to antibody V regions including the idiotype (specific antigen binding region) for the purpose of stimulating idiotype networks.

The type of antigen used for such fusion proteins can also be one that normally induces an allergic response, such as the Der p I and Der p II from dust mites, or tropomyosin from several types of shellfish, which can be fused at the DNA level to the p35 subunit of IL-12 and expressed in the same cell with the p40 subunit. Immunization with such fusion proteins would induce strong Th1 helper cell responses that would be useful in desensitizing the disease-causing Th2 response in atopic patients with allergy.

To demonstrate the expression of a single chain fusion protein, a scFv version of the KS-1/4 antibody was constructed. The 5' end of the protein-encoding portion of fusion gene (an XbaI to AflIII fragment) consists of a leader sequence derived from a mouse k light chain, fused to the mature protein sequence of the KS-1/4 L chain V region. The end of the V region is fused, in frame, to a DNA encoding the simple linker sequence, $(Gly_4Ser)_3$, described by others (Huston and Oppermann, WO 88/09344) followed, in frame, by the sequence encoding the H chain V region of KS-1/4. The 3' end of this scFv contains a XmaI site, compatible with ligation to the 5' end of the human and mouse versions (XmaI to XhoI fragments) of the p35 subunit of IL-12. The final XbaI to XhoI fragments were inserted into the corresponding sites of the same expression vector (pdC) used to express the free IL-12 subunits to give vectors pdC-SCA-hu-p35 and pdC-SCA-mu-p35.

Figure 6A:
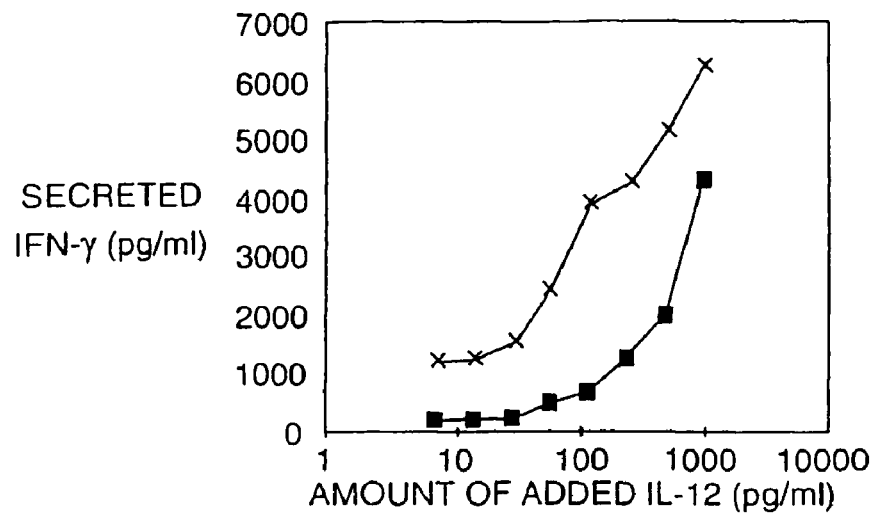
FIG. 6A-B are line graphs depicting the effects of IL-12 (X), single-chain fusion protein with human p35 and p40 subunits (closed squares), and single-chain fusion protein with a mouse p35 subunit and a human p40 subunit (open squares) on induction of IFN-γ secretion.
Figure 6B:
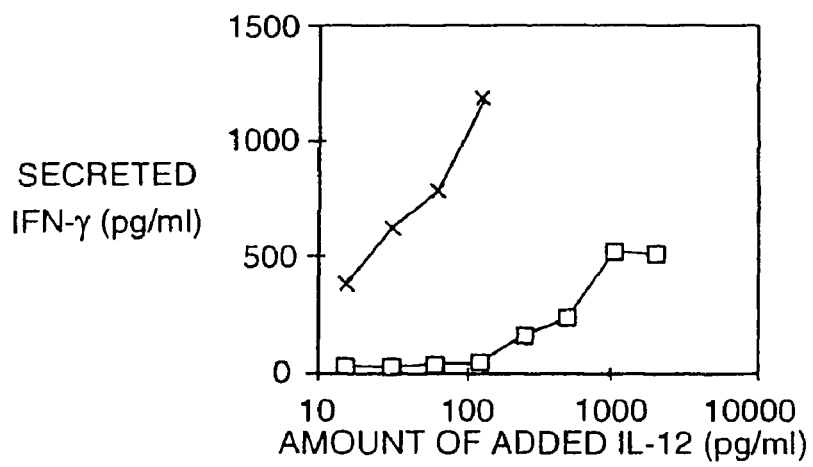
Figure 6C:
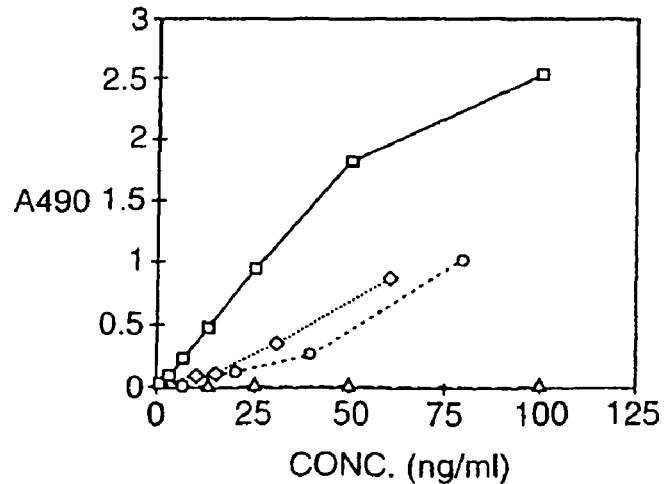
FIG. 6C is line graphs depicting the antigen binding activity of whole Hu-KS-1/4-IL-12 fusion protein (open squares), single-chain fusion protein with human IL-12 (open diamond), single-chain fusion protein with mouse p35 human p40 (open and free circles), and human IL-12 (open triangles)

These vectors were introduced into a human p40 expressing cell line and grown in medium containing methotrexate (0.1 µM). Fusion protein-expressing, drug-resistant clones were identified by ELISA assays specific for the species of p35 utilized in the construct (i.e., an IL-12 human p40 antibody was used for antigen capture, and specific anti-mouse or human-p35 antibodies were used for detection). Culture media from each type of single-chain fusion protein were used to determine their amounts so that relative specific activities could be calculated. Serial dilutions of each sample were tested for the ability to induce IFN-γ secretion as detailed above in Example 2. The results are shown in FIG. 6, which compares the activity of single-chain IL-12 fusion proteins made with either both human subunits or with mouse p35 and human p40, as well as the species specificity of the fusion proteins. The data show that the human IL-12 single chain fusion protein is as active as the whole antibody fusions in its ability, to induce IFN-γ but that it is not as potent as the human IL-12 standard when human PBMC were used (FIG. 6A). The hybrid mouse/human form was approximately 50-fold less than the mouse IL-12 control as was seen with the whole antibody construct (FIG. 6B). FIG. 6C shows an antigen binding assay of the single-chain IL-12 proteins. Plates were coated with the KS antigen recognized by the KS-1/4 antibody and used to capture any reactive antibody or antibody fusion protein. After washing several times, the bound fusion protein was detected using an anti-human IL-12 p40 antibody. The data show that the single-chain fusion proteins bound to the antigen coated plate and could be detected with an antibody against IL-12, thus demonstrating that the fused molecules retain antigen binding activity. The intensity of binding was roughly 3-fold lower than that seen with the whole KS-1/4 antibody but this is not unexpected, due to the monovalency of the single chain construct.

The activity results with both whole antibody and single chain IL-12 fusion proteins suggest that the amino terminus of the p35 chain may be important to receptor binding since fusions appear to reduce activity. Nonetheless, the antibody-IL-12 molecules are still very potent inducers of IFN-γ at concentrations above 1 ng/ml. The concentration of such molecules in treated animals is expected to be several orders of magnitude higher than this both in the circulation, and at the target site of action.

A possible way to increase the specific activity of antibody-IL-12 fusion proteins would be to insert a flexible peptide linker between the antibody and p35 sequences thus giving more freedom to the amino terminal sequences of this subunit. A sequence such as the $(Gly_4Ser)_3$ linker, described above, could be used in this manner. One possible problem with this approach is that such a linker could be immunogenic, especially when fused to a powerful immune stimulator such as IL-12.

EXAMPLE 6

Pharmacokinetic Properties of IL-12 Fusion Proteins

Figure 7:
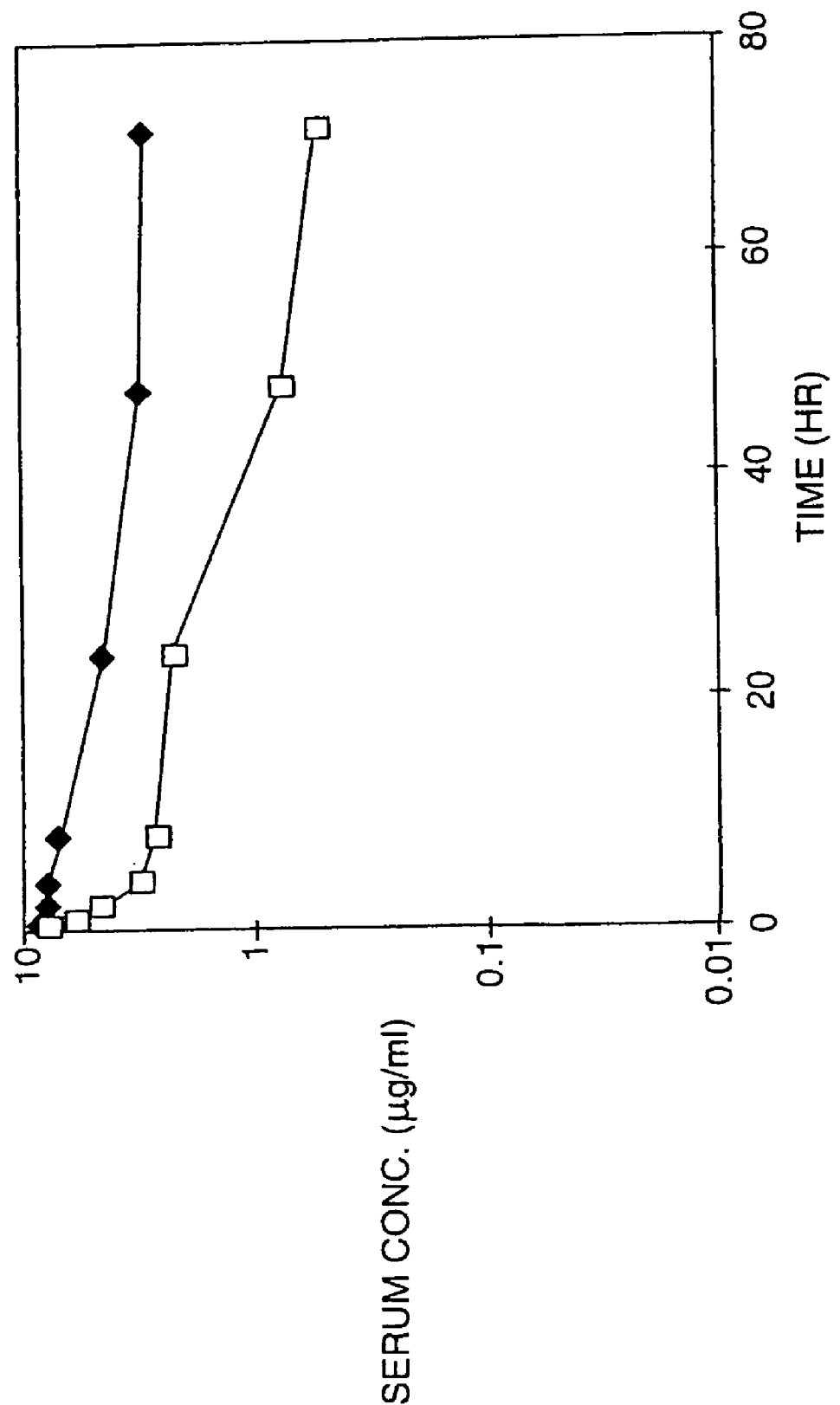
FIG. 7 is a graph depicting the serum half-life of Hu-KS-IL-12 (mouse p35 human p40), as measured by an ELISA using a capture step with anti-human H and L chain and a second detection with either anti-human Fc antibody (closed diamonds) or anti-human IL-12 p40 antibody (open squares)

The antibody-IL-12 fusion proteins were tested for their pharmacokinetic behavior following intravenous injection into Balb/c mice. Blood was collected from mice by retro-orbital bleeding and stored at 4° C. in Eppendorf microcentrifuge tubes. ELISA methods were used to measure the amount of human antibody, as well as the amount of intact IL-12 fusion protein, remaining in the blood at increasing time points. The first ELISA measuring human antibody utilizes an antibody against human H and L chains for capture and an anti-human Fc antibody for detection. The fusion protein-specific assay uses the same first capture step, but an anti-p40 subunit antibody for detection. As depicted in FIG. 7, both the antibody and IL-12 fusion protein had a prolonged half-life but the half-life of the fusion protein was somewhat shorter. This suggests that the circulating fusion protein is cleaved over time to release IL-12 while the antibody remains in the circulation. Earlier-reported experiments with other antibody-cytokine fusion proteins demonstrate that cytokines can be released by protease cleavage. See, Gillies, et al., *Bioconj. Chem.* 4: 230-235 (1993). Nonetheless, the half-lives of the fusion proteins are far longer than the 3 hr value reported for native IL-12. In fact, the serum concentration at 72 hr is still much higher than the level required to induce IFN-γ secretion. Trincieri, *Blood* 84: 4008-4027 (1992).

EXAMPLE 7

Treatment of Established Colon Carcinoma with Antibody-IL-12 Fusion Protein

The murine colon carcinoma, CT26, is particularly insensitive to treatment with systemic administration with mouse IL-12 at non-toxic doses. Martinotti, et al., *Eur. J. Immunol.* 25: 137-146 (1995). Some efficacy has been found when systemic IL-12 administration has been combined together with repeated vaccination of irradiated CT26 cells, engineered to secrete IL-2. Vagliani, et al., *Cancer Res.* 56: 467-470 (1996). An alternative approach to successful therapy involved the engineering CT26 to secrete low levels of IL-12. This was ineffective unless mice were first treated with antibodies to deplete CD4+ cells. Martinotti, et al., *Eur. J. Immunol.* 25: 137-146 (1995), presumably due to an immunosuppressive effect of these cells after exposure to the engineered tumors in vivo. Still another approach of engineering much higher IL-12 secretors was far more successful, thus indicating that the amount of local IL-12 was critical in establishing an immune response to subcutaneous tumors, Colombo, et al., *Cancer Res.* 56: 2531-2534 (1996). In this case, however, there was no demonstration of treatment of established, disseminated tumors similar to what would be seen in the clinical setting. The purpose of the present experiment was to evaluate the efficacy of antibody-IL-12 fusion proteins for the treatment of murine colon carcinoma, CT26.

CT26 cells were transfected with a cDNA encoding the antigen recognized by the KS-1/4 antibody, referred to as either KS antigen (KSA) or epithelial cell adhesion molecule (EpCAM). Clones expressing this protein on their surface were identified by immunostaining with KS-1/4 and fluorescence activated cell sorting (FACS) analysis. Cells from one clone, stably expressing KSA (clone 21.6), were injected into the tail vein of Balb/c mice ($1 \times 10^5$ per mouse). Untreated mice formed extensive pulmonary metastases by day 28 and died within 40 days of inoculation. This growth rate was virtually the same as the parental cells indicating that the expression of the human KSA had no effect on CT26 immunogenicity or ability to form tumors.

The efficacy of the antibody-IL-12 fusion protein for therapy of CT26 metastases was tested in this mouse model using the hybrid human/mouse form which has activity on mouse cells. Following tumor cell injection, mice received injections of either PBS (no treatment control), the KS-1/4-IL-2 fusion protein (positive control), KS-1/4 antibody with free IL-2 (negative control) or the KS-1/4-IL-12 fusion protein (test sample). Treatment began on day 4, a time when established metastases are readily detectable by histological staining in the lungs of animals, and continued daily for 5 days. On day 28 after tumor cell inoculation, animals were euthanized and their lungs examined for the presence of tumor. The weights of the lungs were also measured to determine the amount of tumor mass, relative to tumor-free mice. The results are summarized in Table 2. Untreated animals had extensive metastatic disease characterized by near complete surface coverage of the organ with tumor via fusion of individual metastatic nodules. The weights of the lungs increased by an average of three-fold, indicating that the tumor masses actually made tip the majority of the organ. Treated animals had little if any evidence of metastases, with some animals completely free of tumor. None of the animals showed any overt sign of toxicity during the treatment process. Thus, unlike treatment with systemic IL-12, antibody-IL-12 fusion protein therapy can eradicate established metastatic CT26 colon carcinoma.

TABLE 2

Treatment of Murine Colon Carcinoma Lung Metastases in SCID Mice with Antibody-IL-12 Fusion Proteins

| Treatment | Metastatic Score | Organ Weights |
| --- | --- | --- |
| PBS | 3, 3, 3, 3, 3, 3 | 0.52 |
| Hu-KS1/4 | 3, 3, 3, 3, 3 | 0.48 |
| Hu-KS-1/4 + IL-2 | 3, 3, 3, 3, 3 | 0.40 |
| Hu-KS-IL-2 | 2, 1, 1, 1, 1 | 0.22 |
| Hu-KS-IL-12 | 1, 1, 1, 1, 1 | 0.20 |

Experimental lung metastases were induced by intravenous injection of $10^5$ CT26-KSA cells. Treatment began three days later with intravenous injection of 10 μg of the humanized KS-1/4 antibody or the indicated fusion protein for five consecutive days.
Animals were sacrificed and the metastatic score was determined by the extent of surface coverage: 0 = no visible metastatic foci; 1 = less than 5% of the surface covered; 2 = 5 to 50% of the surface covered; and 3 = more than 50% of the lung surface is covered with metastatic foci.

EXAMPLE 8

IL-12 Fusion Proteins as Vaccines

The humanized KS-1/4 antibody IL-12 fusion protein in PBS buffer, made with the murine p35 subunit (HuKS-1/4-mIL-12), was injected into Balb/c mice intravenously (5 μg/day×5). Control mice received the same antibody, in the same amounts, but with no attached IL-12. Neither injection solution contained any other type of adjuvant. On day 10, blood samples were collected into microcentrifuge tubes by retro-orbital bleeding and plasma were prepared by collecting blood samples in plastic tubes containing sodium citrate, followed by centrifugation at full speed in an Eppendorf tabletop microcentrifuge. ELISA plates (96-well) were coated with the HuKS-1/4 protein containing human constant region and used to capture any mouse antibodies made in response to the immunization. After washing away unbound material, the bound mouse antibodies were detected with goat anti-mouse Fc antibody (Jackson ImmunoResearch) coupled to horse-radish peroxidase. Any bound antibodies could be directed to either the human constant regions or the variable region, both of which are shared between the HU-KS-1/4 and the fusion proteins.

Figure 8A:
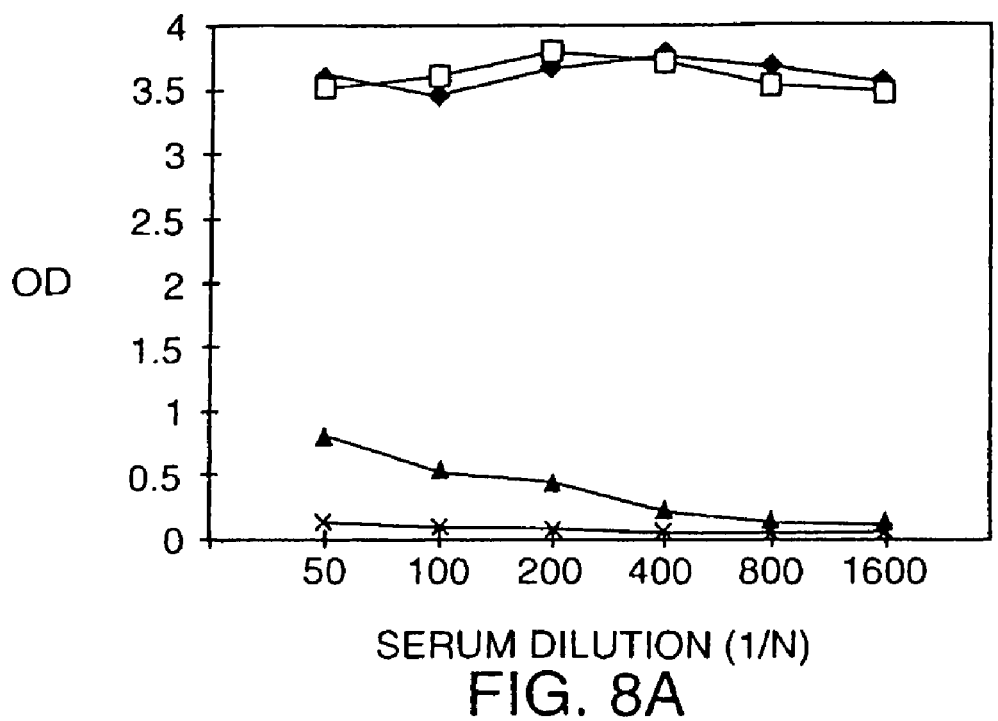
FIG. 8 (top and bottom panels) are line graphs depicting the immunogenicity of IL-12 fusion proteins. Serum dilutions from animals injected with either Hu-KS-1/4 antibody or Hu-KS-1/4-IL-12 (mouse p353 human p40) were tested for reactivity to Hu-KS-1/4 antibody.
Figure 8B:
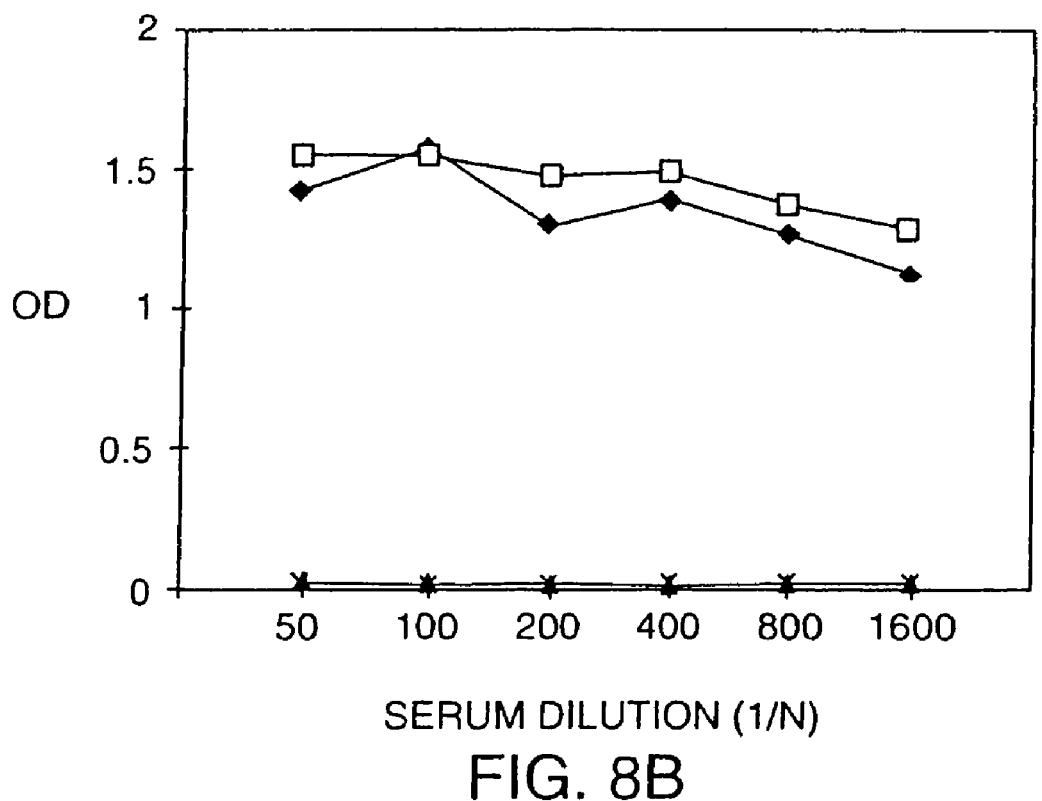

As depicted in FIG. 8, there was little or no reactivity to Hu-KS-1/4 without fused IL-12. The fusion protein, on the other hand, induced a strong antibody response in the absence of exogenous adjuvants and despite the fact that the intravenous route of administration is highly unfavorable for inducing such responses, compared to either subcutaneous or intraperitoneal administration. Antibodies of the IgG2a isotype, which are typical of IL-12 enhanced responses, were seen in the antibody-IL-12 injected group but not the group injected with the Hu-KS-1/4 antibody.

The immunogenicity of IL-12 fusion proteins administered by various routes is tested by injecting a solution of the fusion protein (such as that described above) in PBS or other biocompatible buffer, or a known adjuvant such as Freund's incomplete or complete adjuvant. For example, single or multiple subcutaneous, intradermal or intraperitoneal injections can be given every two weeks. Alternatively, the fusion protein can be administered first by subcutaneous injection and then followed by intraperitoneal injection. Freund's adjuvant cannot be used for human use, due to the irritation at the injection site. Alternative adjuvants such as precipitates of aluminum hydroxide (Alum) are approved for human use and can be used in the present invention. New organic chemical adjuvants based on squalenes and lipids can also be used for injections into the skin.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of selectively delivering interleukin-12 (IL-12) to a target antigen in a mammal comprising the step of:
administering to a mammal a fusion protein comprising an immunoglobulin (Ig) moiety linked by a peptide bond to the p35 and p40 subunits of IL-12, the Ig moiety comprising a variable region specific for a target antigen, wherein IL-12 is selectively delivered to the target antigen.

2. The method of claim 1, wherein the Ig moiety comprises a single-chain Fv moiety.

3. A method of selectively delivering interleukin-12 (IL-12) to a target antigen in a mammal comprising the step of:
administering to a mammal a fusion protein comprising an immunoglobulin (Ig) moiety linked by a peptide bond to the p35 subunit of IL-12, the p35 subunit of IL-12 being linked to the p40 subunit of IL-12, the Ig moiety comprising a variable region specific for a target antigen, wherein IL-12 is selectively delivered to the target antigen.

* * * * *

UNITED STATES PATENT AND TRADEMARK OFFICE
CERTIFICATE OF CORRECTION

| | | |
|---|---|---|
| PATENT NO. | : 7,879,319 B2 | |
| APPLICATION NO. | : 12/498491 | |
| DATED | : February 1, 2011 | |
| INVENTOR(S) | : Stephen D. Gillies et al. | |

It is certified that error appears in the above-identified patent and that said Letters Patent is hereby corrected as shown below:

Title page 1, in the section entitled "Assignee," replace "Merk" with --Merck--.

Signed and Sealed this
Fifth Day of April, 2011

David J. Kappos
*Director of the United States Patent and Trademark Office*